US009090585B2

(12) United States Patent
DeWitt

(10) Patent No.: US 9,090,585 B2
(45) Date of Patent: Jul. 28, 2015

(54) 2,6-DIOXO-3-DEUTERO-PIPERDIN-3-YL-ISOINDOLINE COMPOUNDS

(75) Inventor: Sheila DeWitt, Auburn, NH (US)

(73) Assignee: DeuteRx, LLC, Andover, MA (US)

( * ) Notice: Subject to any disclaimer, the term of this patent is extended or adjusted under 35 U.S.C. 154(b) by 321 days.

(21) Appl. No.: 13/432,382

(22) Filed: Mar. 28, 2012

(65) Prior Publication Data

US 2012/0252844 A1        Oct. 4, 2012

Related U.S. Application Data

(60) Provisional application No. 61/468,179, filed on Mar. 28, 2011.

(51) Int. Cl.
*C07D 401/00* (2006.01)
*A61K 31/445* (2006.01)
*C07D 401/04* (2006.01)

(52) U.S. Cl.
CPC .................................... *C07D 401/04* (2013.01)

(58) Field of Classification Search
USPC ................................ 514/323, 200; 546/200
See application file for complete search history.

(56) References Cited

U.S. PATENT DOCUMENTS

| 5,635,517 | A | 6/1997 | Muller et al. |
| 5,955,476 | A | 9/1999 | Muller et al. |
| 6,221,335 | B1 | 4/2001 | Foster |
| 6,334,997 | B1 | 1/2002 | Foster et al. |
| 6,440,710 | B1 | 8/2002 | Keinan et al. |
| 6,603,008 | B1 | 8/2003 | Ando et al. |
| 7,091,353 | B2 | 8/2006 | Robarge et al. |
| 7,189,740 | B2 | 3/2007 | Zeldis |
| 7,393,863 | B2 | 7/2008 | Zeldis |
| 7,459,466 | B2 | 12/2008 | Muller et al. |
| 7,465,800 | B2 | 12/2008 | Jaworsky et al. |
| 7,517,990 | B2 | 4/2009 | Ito et al. |
| 7,576,104 | B2 | 8/2009 | Robarge et al. |
| 7,635,700 | B2 | 12/2009 | Muller et al. |
| 7,820,697 | B2 | 10/2010 | Man et al. |
| 8,012,997 | B2 | 9/2011 | Robarge et al. |
| 8,288,414 | B2 | 10/2012 | Czarnik |
| 8,288,537 | B2 | 10/2012 | Golec et al. |
| 8,481,568 | B2 | 7/2013 | Muller et al. |
| 8,492,395 | B2 | 7/2013 | Muller et al. |
| 8,518,972 | B2 | 8/2013 | Man et al. |
| 8,669,276 | B2 | 3/2014 | Czarnik |
| 2003/0096841 | A1 | 5/2003 | Robarge et al. |
| 2007/0004920 | A1 | 1/2007 | Ge et al. |
| 2007/0049618 | A1 | 3/2007 | Muller et al. |
| 2007/0066512 | A1 | 3/2007 | Verhelle et al. |
| 2007/0082929 | A1 | 4/2007 | Gant et al. |
| 2007/0197695 | A1 | 8/2007 | Potyen et al. |
| 2008/0199422 | A1 | 8/2008 | Zeldis |
| 2009/0022706 | A1 | 1/2009 | Gant et al. |
| 2009/0054433 | A1 | 2/2009 | Nam et al. |
| 2009/0069379 | A1 | 3/2009 | Czarnik |
| 2009/0082375 | A1 | 3/2009 | Cameron et al. |
| 2009/0093504 | A1 | 4/2009 | Muller et al. |
| 2009/0317385 | A1 | 12/2009 | Brady et al. |
| 2010/0016342 | A9 | 1/2010 | Cameron et al. |
| 2011/0196150 | A1 | 8/2011 | Man et al. |
| 2012/0230982 | A1 | 9/2012 | Zhou et al. |
| 2012/0232100 | A1 | 9/2012 | Muller et al. |
| 2012/0302605 | A1 | 11/2012 | DeWitt |
| 2012/0322073 | A1 | 12/2012 | Lopez-Girona et al. |
| 2012/0322799 | A1 | 12/2012 | Damodara |
| 2013/0274291 | A1 | 10/2013 | DeWitt |
| 2014/0142141 | A1 | 5/2014 | Czarnik |

FOREIGN PATENT DOCUMENTS

| WO | WO-95/26325 A2 | 10/1995 |
| WO | WO-95/26325 A3 | 12/1995 |
| WO | WO 99/47512 * | 9/1999 |
| WO | WO-02/059106 A1 | 8/2002 |
| WO | WO-02/094180 A2 | 11/2002 |
| WO | WO-2006/053160 A2 | 5/2006 |
| WO | WO-2006/127938 A1 | 11/2006 |
| WO | WO-2007/027527 A2 | 3/2007 |
| WO | WO-2007/136640 A2 | 11/2007 |
| WO | 2008/027542 A2 | 3/2008 |
| WO | 2008/033567 A1 | 3/2008 |
| WO | WO-2008/039489 A2 | 4/2008 |
| WO | 2008/115516 A2 | 9/2008 |
| WO | WO-2009/042177 A1 | 4/2009 |
| WO | WO-2009/042200 A1 | 4/2009 |
| WO | WO-2009/085234 A9 | 7/2009 |
| WO | WO-2009/097120 A1 | 8/2009 |
| WO | WO-2009/105256 A2 | 8/2009 |
| WO | WO-2009/139880 A1 | 11/2009 |
| WO | 2009/145899 A1 | 12/2009 |

(Continued)

OTHER PUBLICATIONS

PCT/US12/30870 International Search Report and Written Opinion Jul. 9, 2012 (corresponding PCT application).
Buteau, K., "Deuterated Drugs: Unexpectedly Nonobvious?", 10 J. High Tech. L. 22 (2009).
Foster, A., "Deuterium Isotope Effects in the Metabolism of Drugs and Xenobiotics: Implications for Drug Design", Adv. Drug Res., 14:2-40 (1985).
Foster, "Deuterium isotope effects in studies of drug metabolism", TIPS, Dec. 1984, 524-527.
Harbeson et al., "Deuterium in Drug Discovery and Development", Annual Reports in Med Chem, 46:403-417 (2011).
Hutt et al., The Chiral Switch: The Development of Single Enantiomer Drugs from Racemates, ACTA Facult. Pharm. Univ. Comenianae, 50:7-23 (2003).
Kaufman et al., "Deuterium Enrichment of Vitamin A at the C20 Position Slows the Formation of Detrimental Vitamin A Dimers in Wild-type Rodents", J. Biol. Chem., 286(10):7958-7965 (2011).
Maltais et al., "In Vitro and In Vivo Isotope Effects with Hepatitis C Protease Inhibitors: Enchanced Plasma Exposure of Deuterated Telaprevir versus Telaprevir in Rats", J. Med. Chem., 52:7993-8001 (2009).

(Continued)

*Primary Examiner* — John Mabry
(74) *Attorney, Agent, or Firm* — Goodwin Procter LLP

(57) ABSTRACT

The present application describes 2-(2',6'-dioxo-3'-deutero-piperidin-3'-yl)isoindoles, deuterated derivatives thereof, stereoisomers thereof, pharmaceutically acceptable salt forms thereof, and methods of treating using the same.

23 Claims, No Drawings

(56) References Cited

FOREIGN PATENT DOCUMENTS

| WO | 2010/053732 A1 | 5/2010 |
|---|---|---|
| WO | WO-2010/056344 A1 | 5/2010 |
| WO | WO-2010/093434 A1 | 8/2010 |
| WO | WO-2010/093605 A1 | 8/2010 |
| WO | WO-2009/105256 A3 | 11/2010 |
| WO | WO-2011/079091 A1 | 6/2011 |
| WO | 2011/100380 A1 | 8/2011 |
| WO | WO-2012/027065 A2 | 3/2012 |
| WO | WO-2012/068512 A1 | 5/2012 |
| WO | WO-2012/125438 A1 | 9/2012 |
| WO | WO-2012/125459 A1 | 9/2012 |
| WO | WO-2012/125475 A1 | 9/2012 |
| WO | WO-2012/135299 A1 | 10/2012 |
| WO | WO-2012/149299 A2 | 11/2012 |
| WO | WO-2014/004990 A2 | 1/2014 |
| WO | WO-2014/025958 A2 | 2/2014 |
| WO | WO-2014/025964 A2 | 2/2014 |
| WO | WO-2014/025978 A1 | 2/2014 |
| WO | WO-2014/039421 A1 | 3/2014 |
| WO | WO-2014/039960 A1 | 3/2014 |
| WO | WO-2014/110558 A1 | 7/2014 |

OTHER PUBLICATIONS

Mislow et al., "A Note on Steric Isotope Effects. Conformational Kinetic Isotope Effects in the Racemization of 9,10-Dihydro-4,5-Dimethylphenanthrene", JACS, 85:1199-1200 (1963).
Nassar et al., "Improving the decision-making process in the structural modification of drug candidates: enhancing metabolic stability", DDT, 9(23):1020-1028 (2004).
Nelson et al., "The Use of Deuterium Isotope Effects to Probe the Active Site Properties, Mechanism of Cytochrome P450-Catalyzed Reactions, and Mechanisms of Metabolically Dependent Toxicity", DMD, 31(12):1481-1498 (2003).
Shao et al., "Derivatives of tramadol for increased duration of effect", Bioorg. Med. Chem. Lett. 16:691-694 (2006).
Shao et al., "The Kinetic Isotope Effect in the Search for Deuterated Drugs", Drug News & Perspectives, 23(6):398-404 (2010).
Stedman et al., "Review article: comparison of the pharmacokinetics, acid suppression and efficacy of proton pump inhibitors", Aliment Pharmacol. Ther., 14:963-978 (2000).
Wiberg, K., "The Deuterium Isotope Effect", Chem. Rev., 55(4):713-743 (1955).
Yarnell, A., "Heavy-Hydrogen Drugs Turn Heads, Again", Chemical & Engineering News, 87(25):36-39 (2009).
Zhu et al., "Deuterated Clopidogrel Analogues as a New Generation of Antiplatelet Agents", ACS Med. Chem. Lett., (2013) (4 pages).
Yamamoto, Takeshi et al., Synthesis and Configurational Stability of (S)- and (R)-Deuteriothalidomides, Chem. Pharm. Bull. 2010, 58(1), 110-112.
Takeuchi, Yoshio et al., (R)- and (S)-3-Fluorothalidomies: Isosteric Analogues of Thalidomide, Organic Letters 1999, 1(10), 1571-1573.
Man, Hon-Wah et al., a-Fluoro-Substituted Thalidomide Analogues, Biorg. & Med. Chem. Lett. 2003, 13, 3415-3417.
Chemical Database Search Results, 3 pages (2011).
International Search Report and Written Opinion for PCT/US2011/061485 dated Apr. 5, 2012.
International Search Report and Written Opinion for PCT/US2014/027918 dated Jul. 28, 2014.
International Search Report and Written Opinion for PCT/US2014/011440 dated Apr. 25, 2014.
Teo et al., "Chiral inversion of the second generation IMiD™ CC-4047 (ACTIMID™) in human plasma and phosphate-buffered saline", *Chirality*, 2003, 15(4), 348-351 (Abstract).
CoNCERT Pharmaceuticals, Inc. (2007) "Precisional Deuterium Chemistry Backgrounder," 6 pages.
Extended European Search Report for EP 12764895 dated Oct. 17, 2014 (9 pages).

* cited by examiner

2,6-DIOXO-3-DEUTERO-PIPERDIN-3-YL-ISOINDOLINE COMPOUNDS

CROSS-REFERENCE TO RELATED APPLICATIONS

The present application claims priority benefit under 35 U.S.C. §119(e) of U.S. Provisional Patent Application Ser. No. 61/468,179 filed 28 Mar. 2011. The disclosure of this application is incorporated herein by reference.

BACKGROUND OF THE INVENTION 2-(2',6'-Dioxopiperidin-3'-yl)isoindoles, Formula A shown below, are derivatives of thalidomide and are currently being studied as immunomodulators.

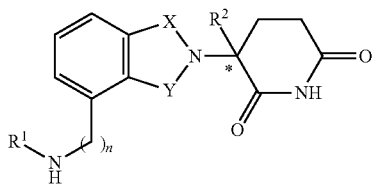

A

The compounds of the above formula, including N-((2-(2',6'-dioxopiperidin-3'-yl)-1,3-dioxoisoindolin-4-yl)methyl)cyclopropanecarboxamide, are described in U.S. Pat. Nos. 7,091,353; 7,189,740; 7,393,863; and, 7,576,104; the contents of which are incorporated herein by reference.

The compounds of Formula A, because of the asymmetric 3' carbon on the glutarimide ring (2',6'-dioxopiperidinyl ring), is a racemic mixture of R and S stereoisomers. The hydrogen at the 3' position is acidic due to the presence of the adjacent carbonyl moiety, thereby making it difficult to separate the two stereoisomers and difficult to determine if one of the stereoisomers is superior to the other.

WO2010/093604 describes isotopologues of thalidomide but does not describe deuteration at the asymmetric carbon of its glutarimide ring.

WO2010/093434 describes isotopologues of lenalidomide but does not describe deuteration at the asymmetric carbon of its glutarimide ring.

WO2008/027542 and WO2009/145899 describe 5-substituted isoindolines, but neither describes deuteration at the asymmetric carbon of its glutarimide ring. The disclosures of these applications are incorporated herein by reference.

WO2008/033567 describes N-methylaminomethyl isoindoles, but does not describe deuteration at the asymmetric carbon of its glutarimide ring. The disclosure of this application is incorporated herein by reference.

WO2008/115516, WO2010/053732, and WO2011/100380 describe 4'-O-substituted isoindolines, isoindolines, and arylmethoxy isoindolines, respectively, but do not describe deuteration at the asymmetric carbon of their respective glutarimide rings. The disclosures of these applications are incorporated herein by reference.

Since 2-(2',6'-dioxopiperidin-3'-yl)isoindoles are known and useful pharmaceutical compounds, it is desirable to discover novel derivatives thereof.

SUMMARY OF THE INVENTION

Accordingly, described herein are 2-(2',6'-dioxo-3'-deutero-piperidin-3'-yl)isoindoles or a stereoisomer or pharmaceutically acceptable salt thereof.

Another aspect provided herein is a pharmaceutical composition comprising a pharmaceutically acceptable carrier and a therapeutically effective amount of at least one of the deutero-compounds of the invention or a pharmaceutically acceptable salt thereof.

Another aspect is a method for treating multiple myeloma, comprising administering to a host in need of such treatment a therapeutically effective amount of at least one of the deutero-compounds of the invention or a pharmaceutically acceptable salt thereof.

Also provided are novel 2-(2',6'-dioxo-3'-deutero-piperidin-3'-yl)isoindoles or a stereoisomer or pharmaceutically acceptable salt thereof for use in therapy.

Another aspect is the use of novel 2-(2',6'-dioxo-3'-deutero-piperidin-3'-yl)isoindoles or a stereoisomer or pharmaceutically acceptable salt thereof for the manufacture of a medicament (e.g., for the treatment of myelodysplastic syndrome).

These and other aspects, which will become apparent during the following detailed description, have been achieved by the inventor's discovery of 2-(2',6'-dioxo-3'-deutero-piperidin-3'-yl)isoindoles.

DETAILED DESCRIPTION OF PREFERRED EMBODIMENTS

Deuterium (D or $^2$H) is a stable, non-radioactive isotope of hydrogen and has an atomic weight of 2.0144. Hydrogen naturally occurs as a mixture of the isotopes $^1$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their non-enriched counterparts. Thus, the present invention relates to a deuterium enriched compound or compounds whose enrichment is greater than naturally occurring deuterated molecules.

All percentages given for the amount of deuterium present are mole percentages. Further, when a variable is not accompanied by a definition, the previous definition of the variable controls.

[1a] In an aspect, the invention provides a 3'-deutero-compound of formula I or a stereoisomer or pharmaceutically acceptable salt thereof:

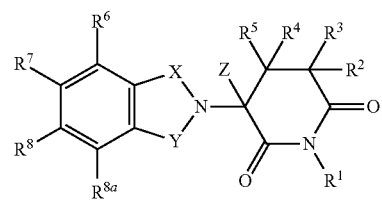

I wherein:
one of $R^8$-$R^{8a}$ is —$(CR^9R^{10})_n$A and the other is selected from H and D;
alternatively, $R^{8a}$ is —$OR^{12a}$, and $R^8$ is selected from H and D;
A is $NR^{11}R^{12}$;
alternatively, when n=1, then A is selected from D, H, and $NR^{11}R^{12}$;

one of X and Y is C=O and the other is selected from $CH_2$, CHD, $CD_2$, and C=O;

Z is H or D, provided that the abundance of deuterium in Z is at least 30%;

$R^1$-$R^7$ and $R^9$-$R^{10}$ are independently selected from H and D;

$R^{11}$ is selected from H, D, and $CH_3$;

$R^{12}$ is selected from H, D, $(C_1$-$C_8)$alkyl, $(C_3$-$C_7)$cycloalkyl, $(C_2$-$C_8)$alkenyl, $(C_2$-$C_8)$alkynyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, $C(O)R^{13}$, $C(S)R^{13}$, $C(O)OR^{14}$, $(C_1$-$C_8)$alkyl-$N(R^{16})_2$, $(C_1$-$C_8)$alkyl-$OR^{15}$, $(C_1$-$C_8)$alkyl-$C(O)OR^{15}$, $C(O)NHR^{13}$, $C(S)NHR^{13}$, $C(O)NR^{13}R^{13'}$, $C(S)NR^{13}R^{13'}$, and $(C_1$-$C_8)$alkyl-$O(CO)R^{15}$;

provided that when n=0, $R^{12}$ is other than H or D;

$R^{12a}$ is selected from $CH_2$—$R^a$—$R^b$—$R^c$, H, $(C_1$-$C_8)$alkyl, $(C_2$-$C_8)$alkenyl, $(C_2$-$C_8)$alkynyl, $(C_0$-$C_4)$alkyl-$(C_3$-$C_7)$cycloalkyl, $C(O)(C_1$-$C_8)$alkyl, $C(O)O(C_1$-$C_8)$alkyl, $C(O)NH(C_1$-$C_8)$alkyl, $C(O)N((C_1$-$C_8)$alkyl$)_2$, $C(O)(C_3$-$C_7)$cycloalkyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, C(O)aryl, $C(O)(C_1$-$C_6)$heterocycloalkyl, and $C(O)(C_2$-$C_9)$heteroaryl, and $R^{12a}$ is optionally substituted with 1-3 groups selected from $(C_1$-$C_6)$alkyl, $(C_1$-$C_6)$haloalkyl, $(C_1$-$C_6)$alkoxy, $(C_1$-$C_6)$haloalkoxy, =O, $NR^{20}_2$, $CO_2R^{20}$, $C(O)NH(C_1$-$C_8)$alkyl, $C(O)N((C_1$-$C_8)$alkyl$)_2$, $NO_2$, —CN, OH, halogen, and $S(O)_2(C_1$-$C_8)$alkyl;

$R^a$ is a bond, alternatively, $R^a$ is selected from aryl, $(C_1$-$C_6)$heterocycloalkyl, and $(C_2$-$C_9)$heteroaryl, wherein $R^a$ is optionally substituted with 1-3 halogen;

$R^b$ is selected from $(CH_2)_m$, $O(CH_2)_m$, and $(CH_2)_mO$;

m is selected from 0-3;

$R^c$ is selected from aryl, $(C_1$-$C_6)$heterocycloalkyl, and $(C_2$-$C_9)$heteroaryl, and $R^c$ is substituted 0-2 groups selected from $(C_1$-$C_6)$alkyl, $(C_1$-$C_6)$haloalkyl, $(C_1$-$C_6)$alkoxy, $(C_1$-$C_6)$haloalkoxy, =O, $NR^{20}_2$, $CO_2R^{20}$, —CN, OH, halogen, $S(O)_2(C_1$-$C_8)$alkyl, aryl substituted with 0-2 $R^d$, and $(C_2$-$C_9)$heteroaryl substituted with 0-2 $R^d$;

$R^d$ is selected from $(C_1$-$C_6)$alkyl, $(C_1$-$C_6)$haloalkyl, $(C_1$-$C_6)$alkoxy, $(C_1$-$C_6)$haloalkoxy, halogen, $CONR^{20}_2$, $CO_2(C_1$-$C_6)$alkyl, and $CO_2(C_1$-$C_6)$haloalkyl;

$R^{13}$ is selected from H, $(C_1$-$C_8)$alkyl, $(C_3$-$C_7)$cycloalkyl, $(C_2$-$C_8)$alkenyl, $(C_2$-$C_8)$alkynyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, $(C_0$-$C_8)$alkyl-$N(R^{16})_2$, $(C_1$-$C_8)$alkyl-$OR^{15}$, $(C_1$-$C_8)$alkyl-$C(O)OR^{15}$, $(C_1$-$C_8)$alkyl-$O(CO)R^{15}$, and $C(O)OR^{15}$;

$R^{13'}$ is selected from $(C_1$-$C_8)$alkyl, $(C_3$-$C_7)$cycloalkyl, $(C_2$-$C_8)$alkenyl, $(C_2$-$C_8)$alkynyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, $(C_0$-$C_8)$alkyl-$N(R^{16})_2$, $(C_1$-$C_8)$alkyl-$OR^{15}$, $(C_1$-$C_8)$alkyl-$C(O)OR^{15}$, $(C_1$-$C_8)$alkyl-$O(CO)R^{15}$, and $C(O)OR^{15}$;

$R^{14}$ is selected from $(C_1$-$C_8)$alkyl, $(C_2$-$C_8)$alkenyl, $(C_2$-$C_8)$alkynyl, $(C_1$-$C_4)$alkyl-$OR^{15}$, $(C_0$-$C_4)$alkyl-aryl, $(C_0$-$C_4)$alkyl-$(C_1$-$C_6)$heterocycloalkyl, and $(C_0$-$C_4)$alkyl-$(C_2$-$C_9)$heteroaryl;

$R^{15}$ is selected from H, $(C_1$-$C_8)$alkyl, $(C_2$-$C_8)$alkenyl, $(C_2$-$C_8)$alkynyl, $(C_0$-$C_4)$alkyl-aryl, and $(C_2$-$C_9)$heteroaryl;

$R^{16}$, at each occurrence, is independently selected from H, D, $(C_1$-$C_8)$alkyl, $(C_2$-$C_8)$alkenyl, $(C_2$-$C_8)$alkynyl, $(C_0$-$C_4)$alkyl-aryl, $(C_2$-$C_9)$heteroaryl, and $(C_0$-$C_8)$alkyl-$C(O)OR^{15}$;

alternatively, $N(R^{16})_2$ forms a heterocycloalkyl group;

n, at each occurrence, is selected from 0, 1, 2, and 3;

the cycloalkyl, heterocycloalkyl, aryl, and heteroaryl groups are optionally substituted with 1-3 $R^{17}$;

$R^{17}$, at each occurrence, is independently selected from H, D, halogen, $NO_2$, —CN, $(C_1$-$C_8)$alkyl, $(C_1$-$C_6)$haloalkyl, $(C_1$-$C_6)$alkoxy, $(C_1$-$C_6)$haloalkoxy, $(C_1$-$C_6)$alkyenedioxy, —NHC(O)$(C_1$-$C_6)$alkyl, $CH_2OCH_3$, $CH_2CH_2OCH_3$, S—$(C_1$-$C_8)$alkyl, $SO_2(C_1$-$C_8)$alkyl, S—$(C_1$-$C_8)$haloalkyl, $SO_2(C_1$-$C_8)$haloalkyl, $(C_0$-$C_4)$alkyl-$R^{17a}$, $(C_0$-$C_4)$alkyl-$R^{18}$, —O—$(C_0$-$C_4)$alkyl-$R^{18}$, —$(CH_2$—$R^{19})_p$—$R^{18}$, OC(O)$(CH_2)_pNH_2$, and OC(O)$(CH_2)_p(C_1$-$C_6)$heterocycloalkyl;

p, at each occurrence, is selected from 0, 1, and 2;

$R^{17a}$, at each occurrence, is independently selected from OH, $NH_2$, and $CO_2R^{20}$;

$R^{18}$, at each occurrence, is independently selected from aryl, $(C_1$-$C_6)$heterocycloalkyl, and $(C_2$-$C_9)$heteroaryl, wherein each aryl, heterocycloakyl, and heteroaryl is optionally substituted with 1-3 $(C_1$-$C_8)$alkyl;

$R^{19}$, at each occurrence, is independently selected from $CH_2$, NH, and O;

$R^{20}$ is selected from H and $(C_1$-$C_8)$alkyl;

wherein a hydrogen atom present in any of the substituents is optionally replaced by deuterium.

[2a] In another aspect, the present invention provides compounds of formula I or a stereoisomer or pharmaceutically acceptable salt thereof, wherein:

$R^8$ is —$(CR^9R^{10})NR^{11}R^{12}$;

$R^{8a}$ is selected from H and D;

X is $CH_2$;

Y is C=O;

Z is H or D, provided that the abundance of deuterium in Z is at least 30%;

$R^1$-$R^7$ and $R^9$-$R^{10}$ are independently selected from H and D;

$R^{11}$ is selected from H and D;

$R^{12}$ is selected from $C(O)R^{13}$ and $C(O)OR^{14}$;

$R^{13}$ is selected from $(C_1$-$C_8)$alkyl, $(C_0$-$C_4)$alkyl-aryl, $(C_0$-$C_4)$alkyl-$(C_2$-$C_9)$heteroaryl, and $(C_1$-$C_6)$alkyl-$C(O)OR^{15}$;

$R^{14}$ is $(C_1$-$C_8)$alkyl;

$R^{15}$ is selected from H and $(C_1$-$C_8)$alkyl;

the aryl and heteroaryl groups are optionally substituted with 1-3 $R^{17}$;

$R^{17}$, at each occurrence, is independently selected from H, D, halogen, $(C_1$-$C_8)$alkyl, $(C_1$-$C_6)$haloalkyl, $(C_1$-$C_6)$alkoxy, $(C_1$-$C_6)$haloalkoxy, S—$(C_1$-$C_8)$alkyl, and $SO_2(C_1$-$C_8)$alkyl;

wherein a hydrogen atom is present in any of the substituents it is optionally replaced by deuterium.

[3a] In another aspect, the present invention provides compounds of formula I or a stereoisomer or pharmaceutically acceptable salt thereof, wherein:

$R^8$ is selected from H and D;

$R^{8a}$ is —$OR^{12a}$;

X is $CH_2$;

Y is C=O;

Z is H or D, provided that the abundance of deuterium in Z is at least 30%;

$R^1$-$R^7$ and $R^9$-$R^{10}$ are independently selected from H and D;

$R^{12a}$ is selected from H, $(C_1$-$C_8)$alkyl, $(C_2$-$C_8)$alkenyl, $(C_2$-$C_8)$alkynyl, $(C_0$-$C_4)$alkyl-$(C_3$-$C_7)$cycloalkyl, $C(O)(C_1$-$C_8)$alkyl, $C(O)O(C_1$-$C_8)$alkyl, $C(O)NH(C_1$-$C_8)$alkyl, $C(O)N((C_1$-$C_8)$alkyl$)_2$, $C(O)(C_3$-$C_7)$cycloalkyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, C(O)aryl, $C(O)(C_1$-$C_6)$heterocycloalkyl, and $C(O)(C_2$-$C_9)$heteroaryl, and $R^{12a}$ is optionally substituted with 1-3 groups selected from $(C_1$-$C_6)$alkyl, $(C_1$-$C_6)$haloalkyl, $(C_1$-$C_6)$alkoxy, $(C_1$-$C_6)$haloalkoxy, $NR^{20}_2$, $CO_2R^{20}$, $C(O)NH(C_1$-$C_8)$alkyl, $C(O)N((C_1$-$C_8)$alkyl$)_2$, $NO_2$, —CN, OH, halogen, and $S(O)_2(C_1$-$C_8)$alkyl;

$R^{20}$ is selected from H and $(C_1$-$C_8)$alkyl;

wherein a hydrogen atom is present in any of the substituents it is optionally replaced by deuterium.

[4a] In another aspect, the present invention provides compounds of formula I or a stereoisomer or pharmaceutically acceptable salt thereof, wherein:
$R^8$ is selected from H and D;
$R^{8a}$ is —$OR^{12a}$
one of X and Y is C=O and the other is selected from $CH_2$, CHD, $CD_2$, and C=O;
Z is H or D, provided that the abundance of deuterium in Z is at least 30%;
$R^1$-$R^7$ and $R^9$-$R^{10}$ are independently selected from H and D;
$R^{12a}$ is $CH_2$—$R^a$—$R^b$—$R^c$;
$R^a$ is a bond, alternatively, $R^a$ is selected from aryl, $(C_1$-$C_6)$heterocycloalkyl, and $(C_2$-$C_9)$heteroaryl, wherein $R^a$ is optionally substituted with 1-3 halogen;
$R^b$ is selected from $(CH_2)_m$, $O(CH_2)_m$, and $(CH_2)_mO$;
m is selected from 0-3;
$R^c$ is selected from aryl, $(C_1$-$C_6)$heterocycloalkyl, and $(C_2$-$C_9)$heteroaryl, and $R^c$ is substituted 0-2 groups selected from $(C_1$-$C_6)$alkyl, $(C_1$-$C_6)$haloalkyl, $(C_1$-$C_6)$alkoxy, $(C_1$-$C_6)$haloalkoxy, =O, $NR^{20}_2$, $CO_2R^{20}$, —CN, OH, halogen, $S(O)_2(C_1$-$C_8)$alkyl, aryl substituted with 0-2 $R^d$, and $(C_2$-$C_9)$heteroaryl substituted with 0-2 $R^d$;
$R^d$ is selected from $(C_1$-$C_6)$alkyl, $(C_1$-$C_6)$haloalkyl, $(C_1$-$C_6)$alkoxy, $(C_1$-$C_6)$haloalkoxy, halogen, $CONR^{20}_2$, $CO_2(C_1$-$C_6)$alkyl, and $CO_2(C_1$-$C_6)$haloalkyl;
wherein a hydrogen atom present in any of the substituents is optionally replaced by deuterium.

[5a] In another aspect, the present invention provides compounds of formula I or a stereoisomer or pharmaceutically acceptable salt thereof, wherein:
$R^8$ is —$(CR^9R^{10})_nNR^{11}R^{12}$;
$R^{8a}$ is selected from H and D;
one of X and Y is C=O and the other is selected from $CH_2$, CHD, $CD_2$, and C=O;
Z is H or D, provided that the abundance of deuterium in Z is at least 30%;
$R^1$-$R^7$ and $R^9$-$R^{10}$ are independently selected from H and D;
$R^{11}$ is selected from H and D;
$R^{12}$ is selected from $C(O)NHR^{13}$ and $C(O)NR^{13}R^{13'}$;
$R^{13}$ is selected from aryl;
$R^{13'}$ is $(C_1$-$C_8)$alkyl;
n, at each occurrence, is selected from 0, 1, 2, and 3;
the aryl group is substituted with 2 $R^{17}$;
$R^{17}$, at each occurrence, is independently selected from H, halogen, $NO_2$, $(C_1$-$C_8)$alkyl, —$NHC(O)(C_1$-$C_6)$alkyl, $(C_0$-$C_4)$alkyl-$R^{17a}$, $(C_0$-$C_4)$alkyl-$R^{18}$, —O—$R^{18}$, —$(CH_2$—$R^{19})_p$—$R^{18}$, $OC(O)(CH_2)_pNH_2$, and $OC(O)(CH_2)_p(C_1$-$C_6)$heterocycloalkyl;
p, at each occurrence, is selected from 0, 1, and 2;
$R^{17a}$, at each occurrence, is independently selected from OH and $NH_2$;
$R^{18}$, at each occurrence, is independently selected from aryl, $(C_1$-$C_6)$heterocycloalkyl, and $(C_2$-$C_9)$heteroaryl, wherein each aryl, heterocycloakyl, and heteroaryl is optionally substituted with 1-3 $(C_1$-$C_8)$alkyl;
$R^{19}$, at each occurrence, is independently selected from $CH_2$, NH, and O;
wherein a hydrogen atom present in any of the substituents is optionally replaced by deuterium.

[6a] In another aspect, the present invention provides compounds of formula I or a stereoisomer or pharmaceutically acceptable salt thereof, wherein:
$R^8$ is selected from H and D;
$R^{8a}$ is —$(CR^9R^{10})A$ is $NR^{11}R^{12}$;
X is $CH_2$;
Y is C=O;
Z is H or D, provided that the abundance of deuterium in Z is at least 30%;
$R^1$-$R^7$ and $R^9$-$R^{10}$ are independently selected from H and D;
$R^{11}$ is $CH_3$;
$R^{12}$ is selected from H, D, $(C_1$-$C_8)$alkyl, $(C_3$-$C_7)$cycloalkyl, $(C_2$-$C_8)$alkenyl, $(C_2$-$C_8)$alkynyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, $C(O)R^{13}$, $C(S)R^{13}$, $C(O)OR^{14}$, $(C_1$-$C_8)$alkyl-$N(R^{16})_2$, $(C_1$-$C_8)$alkyl-$OR^{15}$, $(C_1$-$C_8)$alkyl-$C(O)OR^{15}$, $C(O)NHR^{13}$, $C(S)NHR^{13}$, $C(O)NR^{13}R^{13'}$, $C(S)NR^{13}R^{13'}$, and $(C_1$-$C_8)$alkyl-$O(CO)R^{15}$;
$R^{13}$ is selected from H, $(C_1$-$C_8)$alkyl, $(C_3$-$C_7)$cycloalkyl, $(C_2$-$C_8)$alkenyl, $(C_2$-$C_8)$alkynyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, $(C_0$-$C_8)$alkyl-$N(R^{16})_2$, $(C_1$-$C_8)$alkyl-$OR^{15}$, $(C_1$-$C_8)$alkyl-$C(O)OR^{15}$, $(C_1$-$C_8)$alkyl-$O(CO)R^{15}$, and $C(O)OR^{15}$;
$R^{13'}$ is selected from $(C_1$-$C_8)$alkyl, $(C_3$-$C_7)$cycloalkyl, $(C_2$-$C_8)$alkenyl, $(C_2$-$C_8)$alkynyl, $(C_0$-$C_4)$alkyl-aryl, $(C_0$-$C_4)$alkyl-$(C_1$-$C_6)$heterocycloalkyl, $(C_0$-$C_4)$alkyl-$(C_2$-$C_9)$heteroaryl, $(C_0$-$C_8)$alkyl-$N(R^{16})_2$, $(C_1$-$C_8)$alkyl-$OR^{15}$, $(C_1$-$C_8)$alkyl-$C(O)OR^{15}$, $(C_1$-$C_8)$alkyl-$O(CO)R^{15}$, and $C(O)OR^{15}$;
$R^{14}$ is selected from $(C_1$-$C_8)$alkyl, $(C_2$-$C_8)$alkenyl, $(C_2$-$C_8)$alkynyl, $(C_1$-$C_4)$alkyl-$OR^{15}$, $(C_0$-$C_4)$alkyl-aryl, $(C_0$-$C_4)$alkyl-$(C_1$-$C_6)$heterocycloalkyl, and $(C_0$-$C_4)$alkyl-$(C_2$-$C_9)$heteroaryl;
$R^{15}$ is selected from H, $(C_1$-$C_8)$alkyl, $(C_2$-$C_8)$alkenyl, $(C_2$-$C_8)$alkynyl, $(C_0$-$C_4)$alkyl-aryl, and $(C_2$-$C_9)$heteroaryl;
$R^{16}$, at each occurrence, is independently selected from H, D, $(C_1$-$C_8)$alkyl, $(C_2$-$C_8)$alkenyl, $(C_2$-$C_8)$alkynyl, $(C_0$-$C_4)$alkyl-aryl, $(C_2$-$C_9)$heteroaryl, and $(C_0$-$C_8)$alkyl-$C(O)OR^{15}$;
alternatively, $N(R^{16})_2$ forms a heterocycloalkyl group;
n, at each occurrence, is selected from 0, 1, 2, and 3;
the cycloalkyl, heterocycloalkyl, aryl, and heteroaryl groups are optionally substituted with 1-3 $R^{17}$;
$R^{17}$, at each occurrence, is independently selected from H, D, halogen, $NO_2$, $(C_1$-$C_8)$alkyl, $(C_1$-$C_6)$haloalkyl, $(C_1$-$C_6)$alkoxy, $(C_1$-$C_6)$haloalkoxy, $(C_1$-$C_6)$alkyenedioxy; —NHC(O)$(C_1$-$C_6)$alkyl, $CH_2OCH_3$, $CH_2CH_2OCH_3$, S—$(C_1$-$C_8)$alkyl, $SO_2(C_1$-$C_8)$alkyl, $(C_0$-$C_4)$alkyl-$R^{17a}$, $(C_0$-$C_4)$alkyl-$R^{18}$, —O—$(C_0$-$C_4)$alkyl-$R^{18}$, —$(CH_2$—$R^{19})_p$—$R^{18}$, $OC(O)(CH_2)_pNH_2$, and $OC(O)(CH_2)_p(C_1$-$C_6)$heterocycloalkyl;
p, at each occurrence, is selected from 0, 1, and 2;
$R^{17a}$, at each occurrence, is independently selected from OH, $NH_2$, and $CO_2R^{20}$;
$R^{18}$, at each occurrence, is independently selected from aryl, $(C_1$-$C_6)$heterocycloalkyl, and $(C_2$-$C_9)$heteroaryl, wherein each aryl, heterocycloakyl, and heteroaryl is optionally substituted with 1-3 $(C_1$-$C_8)$alkyl;
$R^{19}$, at each occurrence, is independently selected from $CH_2$, NH, and O;
$R^{20}$ is selected from H and $(C_1$-$C_8)$alkyl;
wherein a hydrogen atom present in any of the substituents is optionally replaced by deuterium.

[7a] In another aspect, the present invention provides compounds of formula I or a stereoisomer or pharmaceutically acceptable salt thereof, wherein:
$R^{12}$ is selected from $C(O)R^{13}$, $C(O)OR^{14}$, $C(O)NHR^{13}$, and $C(O)NR^{13}R^{13'}$;
$R^{13}$ is selected from H, $(C_1$-$C_8)$alkyl, $(C_0$-$C_4)$alkyl-aryl, $(C_0$-$C_4)$alkyl-$(C_2$-$C_9)$heteroaryl, and $(C_0$-$C_8)$alkyl-$N(R^{16})_2$;
$R^{13'}$ is selected from $(C_1$-$C_8)$alkyl, $(C_0$-$C_4)$alkyl-aryl, and $(C_0$-$C_4)$alkyl-$(C_2$-$C_9)$heteroaryl;
$R^{14}$ is selected from $(C_1$-$C_8)$alkyl;
$R^{15}$ is $(C_1$-$C_8)$alkyl;

$R^{16}$, at each occurrence, is independently selected from H, D, $(C_1-C_8)$alkyl, $(C_2-C_8)$alkenyl, $(C_2-C_8)$alkynyl, $(C_0-C_4)$alkyl-aryl, $(C_2-C_9)$heteroaryl, and $(C_0-C_8)$alkyl-C(O)OR$^{15}$;

the aryl and heteroaryl groups are optionally substituted with 1-3 $R^{17}$;

$R^{17}$, at each occurrence, is independently selected from halogen, $(C_1-C_8)$alkyl, $(C_1-C_6)$haloalkyl, $(C_1-C_6)$alkoxy, $(C_1-C_6)$haloalkoxy, and $(C_1-C_6)$alkyenedioxy;

wherein a hydrogen atom present in any of the substituents is optionally replaced by deuterium.

[8a] In another aspect, the present invention provides compounds of formula I or a stereoisomer or pharmaceutically acceptable salt thereof, wherein:

$R^8$ is —$(CR^9R^{10})_aNR^{11}R^{12}$;
$R^{8a}$ is selected from H and D;
X is $CH_2$;
Y is C=O;
Z is H or D, provided that the abundance of deuterium in Z is at least 30%;
$R^1$-$R^7$ and $R^9$-$R^{10}$ are independently selected from H and D;
$R^{11}$ is selected from H and D;
$R^{12}$ is selected from $(C_0-C_4)$alkyl-aryl, $(C_0-C_4)$alkyl-$(C_2-C_9)$heteroaryl, C(O)R$^{13}$, C(S)R$^{13}$, C(O)OR$^{14}$, C(O)NHR$^{13}$, and C(S)NHR$^{13}$;
$R^{13}$ is selected from $(C_1-C_8)$alkyl, $(C_0-C_4)$alkyl-aryl, $(C_0-C_4)$alkyl-$(C_1-C_6)$heterocycloalkyl, $(C_0-C_4)$alkyl-$(C_2-C_9)$heteroaryl, and $(C_1-C_8)$alkyl-C(O)OR$^{15}$;
$R^{14}$ is selected from $(C_1-C_8)$alkyl;
$R^{15}$ is selected from H and $(C_1-C_8)$alkyl;
n, at each occurrence, is selected from 0 and 1;
the heterocycloalkyl, aryl, and heteroaryl groups are optionally substituted with 1-3 $R^{17}$;
$R^{17}$, at each occurrence, is independently selected from halogen, —CN, $(C_1-C_8)$alkyl, $(C_1-C_6)$haloalkyl, $(C_1-C_6)$alkoxy, $(C_1-C_6)$haloalkoxy, $(C_1-C_6)$alkyenedioxy, S—$(C_1-C_8)$alkyl, $SO_2(C_1-C_8)$alkyl, S—$(C_1-C_8)$haloalkyl, and $SO_2(C_1-C_8)$haloalkyl;
wherein a hydrogen atom present in any of the substituents is optionally replaced by deuterium.

[1] In another aspect, the invention provides a 3'-deutero-compound of formula $I_1$ or a stereoisomer or pharmaceutically acceptable salt thereof:

$I_1$ wherein:
A is $NR^{11}R^{12}$;
alternatively, when n=1, then A is selected from D, H, and $NR^{11}R^{12}$;
one of X and Y is C=O and the other is selected from $CH_2$, CHD, $CD_2$, and C=O;
Z is H or D, provided that the abundance of deuterium in Z is at least 30%;
$R^1$-$R^{11}$ are independently selected from H and D;
$R^{12}$ is selected from H, D, $(C_1-C_8)$alkyl, $(C_3-C_7)$cycloalkyl, $(C_2-C_8)$alkenyl, $(C_2-C_8)$alkynyl, benzyl, $(C_0$-$C_4)$alkyl-$(C_1-C_6)$heterocycloalkyl, $(C_0-C_4)$alkyl-$(C_2-C_5)$heteroaryl, C(O)R$^{13}$, C(S)R$^{13}$, C(O)OR$^{14}$, $(C_1-C_8)$alkyl-N(R$^{16}$)$_2$, $(C_1-C_8)$alkyl-OR$^{15}$, $(C_1-C_8)$alkyl-C(O)OR$^{15}$, C(O)NHR$^{13}$, C(S)NHR$^{13}$, C(O)NR$^{13}$R$^{13'}$, C(S)NR$^{13}$R$^{13'}$, and $(C_1-C_8)$alkyl-O(CO)R$^{15}$;

provided that when n=0, $R^{12}$ is other than H or D;

$R^{13}$ and $R^{13'}$ are independently selected from $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_0-C_8)$alkyl-N(R$^{16}$)$_2$, $(C_1-C_8)$alkyl-OR$^{15}$, $(C_1-C_8)$alkyl-C(O)OR$^{15}$, $(C_1-C_8)$alkyl-O(CO)R$^{15}$, and C(O)OR$^{15}$;

$R^{14}$ is selected from $(C_1-C_8)$alkyl, $(C_2-C_8)$alkenyl, $(C_2-C_8)$alkynyl, $(C_1-C_4)$alkyl-OR$^{15}$, benzyl, aryl, $(C_0-C_4)$alkyl-$(C_1-C_6)$heterocycloalkyl, and $(C_0-C_4)$alkyl-$(C_2-C_5)$heteroaryl;

$R^{15}$ is selected from $(C_1-C_8)$alkyl, $(C_2-C_8)$alkenyl, $(C_2-C_8)$alkynyl, benzyl, aryl, and $(C_2-C_5)$heteroaryl;

$R^{16}$, at each occurrence, is independently selected from H, D, $(C_1-C_8)$alkyl, $(C_2-C_8)$alkenyl, $(C_2-C_8)$alkynyl, benzyl, aryl, $(C_2-C_5)$heteroaryl, and $(C_0-C_8)$alkyl-C(O)OR$^{15}$;

alternatively, $N(R^{16})_2$ forms a heterocycloalkyl group;

n is 0 or 1;

the cycloalkyl, heterocycloalkyl, benzyl, aryl, and heteroaryl groups are optionally substituted with 1-3 $R^{17}$;

$R^{17}$ is selected from H, D, $(C_1-C_8)$alkyl, benzyl, $CH_2OCH_3$, and $CH_2CH_2OCH_3$; and, when a hydrogen atom is present in any of $R^{12}$-$R^{17}$ (e.g., the alkyl, cycloalkyl, alkenyl, alkynyl, benzyl, aryl, heterocycloalkyl, and/or heteroaryl groups) it is optionally replaced by deuterium (e.g., deuterocycloalkyl (e.g., 1-D-cyclopropane), perdeuterocycloalkyl (e.g., $d_5$-cyclopropane), deuteroalkyl (e.g., 1-D-ethane), and perdeuteroalkyl (e.g., perdeuteroethane)).

[2] In another aspect, the present invention provides compounds of formula $I_1$ or a stereoisomer or pharmaceutically acceptable salt thereof, wherein: X and Y are C=O.

[3] In another aspect, the present invention provides compounds of formula $I_1$ or a stereoisomer or pharmaceutically acceptable salt thereof, wherein:

A is $NR^{11}R^{12}$;
n is 0;
$R^{12}$ is selected from $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, C(O)R$^{13}$, C(O)OR$^{14}$, $(C_1-C_8)$alkyl-N(R$^{16}$)$_2$, $(C_1-C_8)$alkyl-OR$^{15}$, $(C_1-C_8)$alkyl-C(O)OR$^{15}$, C(S)NHR$^{13}$, and $(C_1-C_8)$alkyl-O(CO)R$^{15}$;
$R^{13}$ is selected from $(C_1-C_8)$alkyl, $(C_3-C_7)$cycloalkyl, $(C_2-C_8)$alkenyl, $(C_2-C_8)$alkynyl, benzyl, aryl, $(C_0-C_4)$alkyl-$(C_1-C_6)$heterocycloalkyl, $(C_0-C_4)$alkyl-$(C_2-C_5)$heteroaryl, $(C_5-C_8)$alkyl-N(R$^{16}$)$_2$; $(C_0-C_8)$alkyl-NHC(O)OR$^{15}$; $(C_1-C_8)$alkyl-OR$^{15}$, $(C_1-C_8)$alkyl-C(O)OR$^{15}$, $(C_1-C_8)$alkyl-O(CO)R$^{15}$, and C(O)OR$^{15}$.

[4] In another aspect, the present invention provides compounds of formula $I_1$ or a stereoisomer or pharmaceutically acceptable salt thereof, wherein: $R^{12}$ is $(C_1-C_8)$alkyl or benzyl.

[5] In another aspect, the present invention provides compounds of formula $I_1$ or a stereoisomer or pharmaceutically acceptable salt thereof, wherein:

$R^{12}$ is selected from H, D, $(C_1-C_8)$alkyl, benzyl, $CH_2OCH_3$, $CH_2CH_2$, $OCH_3$, and furan-2-yl-$CH_2$—;

provided that when n=0, $R^{12}$ is other than H or D.

[6] In another aspect, the present invention provides compounds of formula $I_1$ or a stereoisomer or pharmaceutically acceptable salt thereof, wherein:

$R^{12}$ is selected from furan-2-yl-$CHR^{17}$— and thien-2-yl-$CHR^{17}$—, wherein the furanyl or thienyl group is substituted with 1-3 $R^{17}$;

provided that when n=0, $R^{12}$ is other than H or D; and, $R^{17}$ is selected from H, D, $(C_1-C_8)$alkyl, benzyl, $CH_2OCH_3$, and $CH_2CH_2OCH_3$.

[7] In another aspect, the present invention provides compounds of formula $I_1$ or a stereoisomer or pharmaceutically acceptable salt thereof, wherein:

$R^{13}$ is selected from $(C_0-C_4)$alkyl-$(C_2-C_5)$heteroaryl, $(C_1-C_8)$alkyl, aryl, and $(C_0-C_4)$alkyl-$OR^5$.

[8] In another aspect, the present invention provides compounds of formula $I_1$ or a stereoisomer or pharmaceutically acceptable salt thereof, wherein:

A is $NR^{11}R^{12}$;
n is 1; and,
$R^{12}$ is $C(O)R^{13}$.

[9] In another aspect, the present invention provides compounds of formula $I_1$ or a stereoisomer or pharmaceutically acceptable salt thereof, wherein:

A is $NR^{11}R^{12}$;
n is 1; and,
$R^{12}$ is $C(O)OR^{14}$.

[10] In another aspect, the present invention provides compounds of formula $I_1$ or a stereoisomer or pharmaceutically acceptable salt thereof, wherein: heteroaryl is selected from pyridyl, furyl, and thienyl.

In another aspect, the present invention provides compounds of formula $I_1$ or a stereoisomer or pharmaceutically acceptable salt thereof, wherein: the H of C(O)NHC(O) is optionally replaced with $(C_1-C_4)$alkyl, aryl, or benzyl.

[11] In another aspect, the present invention provides compounds of formula I or a stereoisomer or pharmaceutically acceptable salt thereof, wherein:

A is $NR^{11}R^{12}$;
X and Y are C=O;
n is 1;
$R^{12}$ is $C(O)R^{13}$; and
$R^{13}$ is selected from $(C_1-C_8)$alkyl and $(C_3-C_7)$cycloalkyl.

[12] In another aspect, the present invention provides compounds of formula $I_1$ or a stereoisomer or pharmaceutically acceptable salt thereof, wherein: $R^{13}$ is $(C_3-C_6)$cycloalkyl.

[13] In another aspect, the present invention provides compounds of formula Ia or a pharmaceutically acceptable salt thereof:

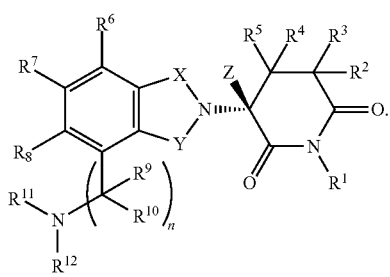

Ia

[14] In another aspect, the present invention provides compounds of formula Ia or a pharmaceutically acceptable salt thereof, wherein:

X and Y are C=O;
n is 1;
$R^{12}$ is $C(O)R^{13}$; and
$R^{13}$ is selected from $(C_1-C_8)$alkyl and $(C_3-C_7)$cycloalkyl.

[15] In another aspect, the present invention provides compounds of formula Ia or a stereoisomer or pharmaceutically acceptable salt thereof, wherein: $R^{13}$ is $(C_3-C_6)$cycloalkyl.

[16] In another aspect, the present invention provides compounds of formula Ia or a stereoisomer or pharmaceutically acceptable salt thereof, wherein: $R^{13}$ is cyclopropyl.

[17] In another aspect, the present invention provides compounds of formula Ia or a pharmaceutically acceptable salt thereof, wherein X and Y are C=O.

[18] In another aspect, the present invention provides compounds of formula Ib or a pharmaceutically acceptable salt thereof:

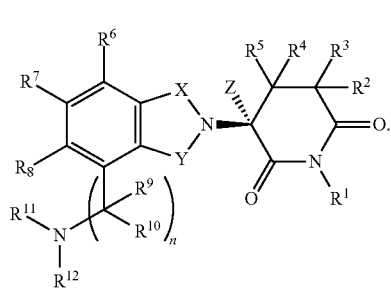

Ib

[19] In another aspect, the present invention provides compounds of formula Ib or a stereoisomer or pharmaceutically acceptable salt thereof, wherein:

X and Y are C=O;
n is 1;
$R^{12}$ is $C(O)R^{13}$; and
$R^{13}$ is selected from $(C_1-C_8)$alkyl and $(C_3-C_7)$cycloalkyl.

[20] In another aspect, the present invention provides compounds of formula Ib or a stereoisomer or pharmaceutically acceptable salt thereof, wherein: $R^{13}$ is $(C_3-C_6)$cycloalkyl.

[21] In another aspect, the present invention provides compounds of formula Ib or a stereoisomer or pharmaceutically acceptable salt thereof, wherein: $R^{13}$ is cyclopropyl.

[22] In another aspect, the present invention provides compounds of formula Ia or a pharmaceutically acceptable salt thereof, wherein X and Y are C=O.

[23] In another aspect, the present invention provides compounds of formula II or a stereoisomer or pharmaceutically acceptable salt thereof, wherein:

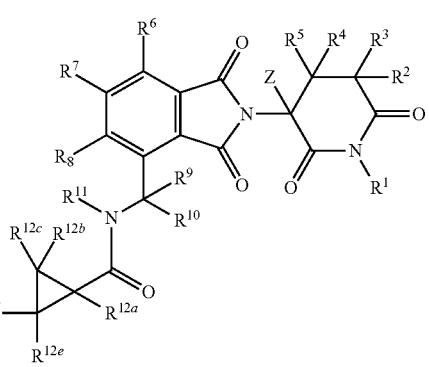

II $R^{12a}$-$R^{12e}$ are independently selected from H and D.

[24] In another aspect, the present invention provides compounds of formula II or a stereoisomer or pharmaceutically acceptable salt thereof, wherein the compound is selected from compounds (a)-(j):

a) $R^1$-$R^{12e}$ are H;
b) $R^1$-$R^{12e}$ are D;
c) $R^2$-$R^3$ are D and the remaining groups are independently selected from H and D;
d) $R^4$-$R^5$ are D and the remaining groups are independently selected from H and D;

e) $R^2$-$R^5$ are D and the remaining groups are independently selected from H and D;
f) $R^6$-$R^8$ are D and the remaining groups are independently selected from H and D;
g) $R^9$-$R^{10}$ are D and the remaining groups are independently selected from H and D;
h) $R^{12a}$ is D and the remaining groups are independently selected from H and D;
i) $R^{12b}$-$R^{12e}$ are D and the remaining groups are independently selected from H and D; and,
j) $R^{12a}$-$R^{12e}$ are D and the remaining groups are independently selected from H and D.

[25] In another aspect, the present invention provides compounds of formula II or a stereoisomer or pharmaceutically acceptable salt thereof, wherein the compound is selected from compounds (k)-(r):
k) $R^2$-$R^3$ are D and the remaining groups are H;
l) $R^4$-$R^5$ are D and the remaining groups are H;
m) $R^2$-$R^5$ are D and the remaining groups are H;
n) $R^6$-$R^8$ are D and the remaining groups are H;
o) $R^9$-$R^{10}$ are D and the remaining groups are H;
p) $R^{12a}$ is D and the remaining groups are H;
q) $R^{12b}$-$R^{12e}$ are D and the remaining groups are H; and,
r) $R^{12a}$-$R^{12e}$ are D and the remaining groups are H.

[26] In another aspect, the present invention provides compounds of formula IIa, or pharmaceutically acceptable salt thereof, wherein:

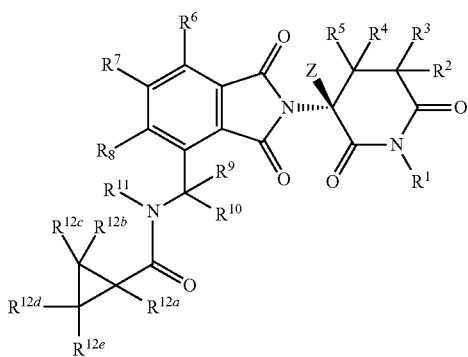

IIa $R^1$-$R^{12e}$ are independently selected from H and D.

[27] In another aspect, the present invention provides compounds of formula IIa, or pharmaceutically acceptable salt thereof, wherein the compound is selected from compounds (a)-(j):
a) $R^1$-$R^{12e}$ are H;
b) $R^1$-$R^{12e}$ are D;
c) $R^2$-$R^3$ are D and the remaining groups are independently selected from H and D;
d) $R^4$-$R^5$ are D and the remaining groups are independently selected from H and D;
e) $R^2$-$R^5$ are D and the remaining groups are independently selected from H and D;
f) $R^6$-$R^8$ are D and the remaining groups are independently selected from H and D;
g) $R^9$-$R^{10}$ are D and the remaining groups are independently selected from H and D;
h) $R^{12a}$ is D and the remaining groups are independently selected from H and D;
i) $R^{12b}$-$R^{12e}$ are D and the remaining groups are independently selected from H and D; and,
j) $R^{12a}$-$R^{12e}$ are D and the remaining groups are independently selected from H and D.

[28] In another aspect, the present invention provides compounds of formula IIa, or pharmaceutically acceptable salt thereof, wherein the compound is selected from compounds (k)-(r):
k) $R^2$-$R^3$ are D and the remaining groups are H;
l) $R^4$-$R^5$ are D and the remaining groups are H;
m) $R^2$-$R^5$ are D and the remaining groups are H;
n) $R^6$-$R^8$ are D and the remaining groups are H;
o) $R^9$-$R^{10}$ are D and the remaining groups are H;
p) $R^{12a}$ is D and the remaining groups are H;
q) $R^{12b}$-$R^{12e}$ are D and the remaining groups are H; and,
r) $R^{12a}$-$R^{12e}$ are D and the remaining groups are H.

[29] In another aspect, the present invention provides compounds of formula IIb, or pharmaceutically acceptable salt thereof, wherein:

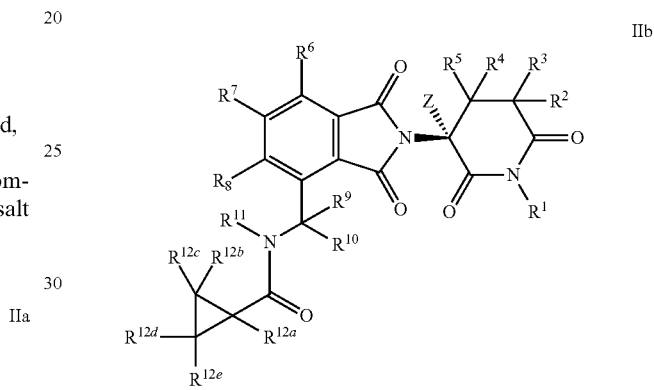

IIb $R^1$-$R^{12e}$ are independently selected from H and D.

[30] In another aspect, the present invention provides compounds of formula IIb, or pharmaceutically acceptable salt thereof, wherein the compound is selected from compounds (a)-(j):
a) $R^1$-$R^{12e}$ are H;
b) $R^1$-$R^{12e}$ are D;
c) $R^2$-$R^3$ are D and the remaining groups are independently selected from H and D;
d) $R^4$-$R^5$ are D and the remaining groups are independently selected from H and D;
e) $R^2$-$R^5$ are D and the remaining groups are independently selected from H and D;
f) $R^6$-$R^8$ are D and the remaining groups are independently selected from H and D;
g) $R^9$-$R^{10}$ are D and the remaining groups are independently selected from H and D;
h) $R^{12a}$ is D and the remaining groups are independently selected from H and D;
i) $R^{12b}$-$R^{12e}$ are D and the remaining groups are independently selected from H and D; and,
j) $R^{12a}$-$R^{12e}$ are D and the remaining groups are independently selected from H and D.

[31] In another aspect, the present invention provides compounds of formula IIb, or pharmaceutically acceptable salt thereof, wherein the compound is selected from compounds (k)-(r):
k) $R^2$-$R^3$ are D and the remaining groups are H;
l) $R^4$-$R^5$ are D and the remaining groups are H;
m) $R^2$-$R^5$ are D and the remaining groups are H;
n) $R^6$-$R^8$ are D and the remaining groups are H;
o) $R^9$-$R^{10}$ are D and the remaining groups are H;

p) $R^{12a}$ is D and the remaining groups are H;
q) $R^{12b}$-$R^{12e}$ are D and the remaining groups are H; and,
r) $R^{12a}$-$R^{12e}$ are D and the remaining groups are H.

[32] In another aspect, the present invention provides compounds wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

[33] In another aspect, the present invention provides compounds of formula $II_1$, or a stereoisomer or pharmaceutically acceptable salt thereof:

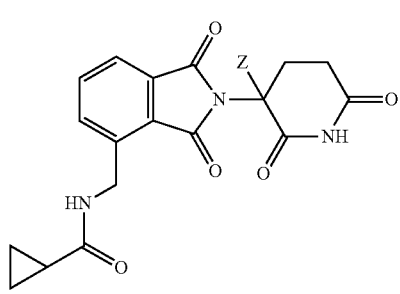

$II_1$ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

[34] In another aspect, the present invention provides compounds of formula $II_1$, or a stereoisomer or pharmaceutically acceptable salt thereof, wherein the abundance of deuterium in Z is at least 80%.

[35] In another aspect, the present invention provides compounds of formula $II_1$, or a stereoisomer or pharmaceutically acceptable salt thereof, wherein the abundance of deuterium in Z is at least 90%.

[36] In another aspect, the present invention provides compounds of formula $II_1$, or a stereoisomer or pharmaceutically acceptable salt thereof, wherein the abundance of deuterium in Z is at least 95%.

[37] In another aspect, the present invention provides compounds of formula $IIa_1$, or pharmaceutically acceptable salt thereof:

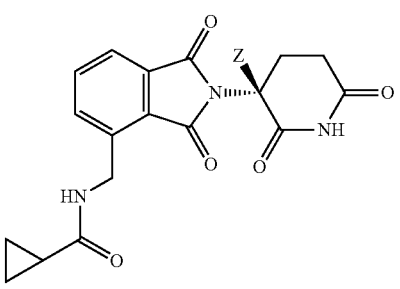

$IIa_1$ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

[38] In another aspect, the present invention provides compounds of formula $IIa_1$, or pharmaceutically acceptable salt thereof, wherein the abundance of deuterium in Z is at least 80%.

[39] In another aspect, the present invention provides compounds of formula $IIa_1$, or pharmaceutically acceptable salt thereof, wherein the abundance of deuterium in Z is at least 90%.

[40] In another aspect, the present invention provides compounds of formula $IIa_1$, or pharmaceutically acceptable salt thereof, wherein the abundance of deuterium in Z is at least 95%.

[41] In another aspect, the present invention provides compounds of formula $IIb_1$, or pharmaceutically acceptable salt thereof:

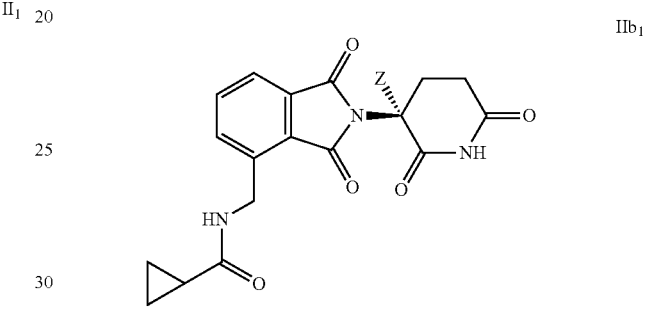

$IIb_1$ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

[42] In another aspect, the present invention provides compounds of formula $IIb_1$, or pharmaceutically acceptable salt thereof, wherein the abundance of deuterium in Z is at least 80%.

[43] In another aspect, the present invention provides compounds of formula $IIb_1$, or pharmaceutically acceptable salt thereof, wherein the abundance of deuterium in Z is at least 90%.

[44] In another aspect, the present invention provides compounds of formula $IIb_1$, or pharmaceutically acceptable salt thereof, wherein the abundance of deuterium in Z is at least 95%.

[45] In another aspect, the present invention provides compounds of formula $I_1$, or a stereoisomer or pharmaceutically acceptable salt thereof, wherein:
n=1; and,
A is selected from D and H.

[46] In another aspect, the present invention provides compound of formula $I_1$ or a stereoisomer or pharmaceutically acceptable salt thereof, wherein the compound is selected from compounds (a)-(g):
a) $R^1$-$R^{10}$ and A are H;
b) $R^1$-$R^{10}$ and A are D;
c) $R^2$-$R^3$ are D and the remaining groups are independently selected from H and D;
d) $R^4$-$R^5$ are D and the remaining groups are independently selected from H and D;
e) $R^2$-$R^5$ are D and the remaining groups are independently selected from H and D;
f) $R^6$-$R^8$ are D and the remaining groups are independently selected from H and D; and, g) R⁹-R¹⁰ and A are D and the remaining groups are independently selected from H and D.

[47] In another aspect, the present invention provides compound of formula I₁ or a stereoisomer or pharmaceutically acceptable salt thereof, wherein the compound is selected from compounds (h)-(n):
h) R¹-R¹⁰ and A are H;
i) R¹-R¹⁰ and A are D;
j) R²-R³ are D and the remaining groups are H;
k) R⁴-R⁵ are D and the remaining groups are H;
l) R²-R⁵ are D and the remaining groups are H;
m) R⁶-R⁸ are D and the remaining groups are H; and,
n) R⁹-R¹⁰ and A are D and the remaining groups are independently selected from H and D.

[48] In another aspect, the present invention provides compound of formula Ic or pharmaceutically acceptable salt thereof:

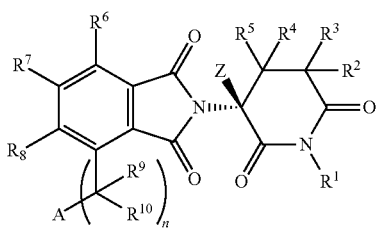

Ic wherein:
n=1; and,
A is selected from H and D.

[49] In another aspect, the present invention provides compound of formula Ic or pharmaceutically acceptable salt thereof, wherein the compound is selected from compounds (a)-(g):
a) R¹-R¹⁰ and A are H;
b) R¹-R¹⁰ and A are D;
c) R²-R³ are D and the remaining groups are independently selected from H and D;
d) R⁴-R⁵ are D and the remaining groups are independently selected from H and D;
e) R²-R⁵ are D and the remaining groups are independently selected from H and D;
f) R⁶-R⁸ are D and the remaining groups are independently selected from H and D; and,
g) R⁹-R¹⁰ and A are D and the remaining groups are independently selected from H and D.

[50] In another aspect, the present invention provides compound of formula Ic or a stereoisomer or pharmaceutically acceptable salt thereof, wherein the compound is selected from compounds (h)-(n):
h) R¹-R¹⁰ and A are H;
i) R¹-R¹⁰ and A are D;
j) R²-R³ are D and the remaining groups are H;
k) R⁴-R⁵ are D and the remaining groups are H;
l) R²-R⁵ are D and the remaining groups are H;
m) R⁶-R⁸ are D and the remaining groups are H; and,
n) R⁹-R¹⁰ and A are D and the remaining groups are independently selected from H and D.

[51] In another aspect, the present invention provides compound of formula Id or pharmaceutically acceptable salt thereof:

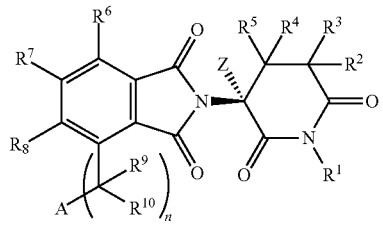

Id wherein:
n=1; and,
A is selected from H and D.

[52] In another aspect, the present invention provides compound of formula Id or pharmaceutically acceptable salt thereof, wherein the compound is selected from compounds (a)-(g):
a) R¹-R¹⁰ and A are H;
b) R¹-R¹⁰ and A are D;
c) R²-R³ are D and the remaining groups are independently selected from H and D;
d) R⁴-R⁵ are D and the remaining groups are independently selected from H and D;
e) R²-R⁵ are D and the remaining groups are independently selected from H and D;
f) R⁶-R⁸ are D and the remaining groups are independently selected from H and D; and,
g) R⁹-R¹⁰ and A are D and the remaining groups are independently selected from H and D.

[53] In another aspect, the present invention provides compound of formula Id or a stereoisomer or pharmaceutically acceptable salt thereof, wherein the compound is selected from compounds (h)-(n):
h) R¹-R¹⁰ and A are H;
i) R¹-R¹⁰ and A are D;
j) R²-R³ are D and the remaining groups are H;
k) R⁴-R⁵ are D and the remaining groups are H;
l) R²-R⁵ are D and the remaining groups are H;
m) R⁶-R⁸ are D and the remaining groups are H; and,
n) R⁹-R¹⁰ and A are D and the remaining groups are independently selected from H and D.

[54] In another aspect, the present invention provides compound of formula I₂ or a stereoisomer or pharmaceutically acceptable salt thereof:

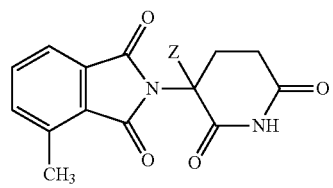

I₂ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

[55] In another aspect, the present invention provides compounds of formula I₂, or pharmaceutically acceptable salt thereof, wherein the abundance of deuterium in Z is at least 80%.

[56] In another aspect, the present invention provides compounds of formula $I_2$, or pharmaceutically acceptable salt thereof, wherein the abundance of deuterium in Z is at least 90%.

[57] In another aspect, the present invention provides compounds of formula $I_2$, or pharmaceutically acceptable salt thereof, wherein the abundance of deuterium in Z is at least 95%.

[58] In another aspect, the present invention provides compound of formula $Ic_1$ or pharmaceutically acceptable salt thereof:

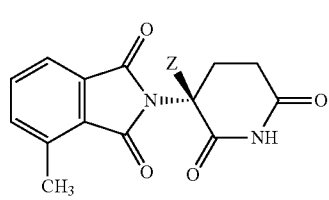

$Ic_1$ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

[59] In another aspect, the present invention provides compounds of formula $Ic_1$, or pharmaceutically acceptable salt thereof, wherein the abundance of deuterium in Z is at least 80%.

[60] In another aspect, the present invention provides compounds of formula $Ic_1$, or pharmaceutically acceptable salt thereof, wherein the abundance of deuterium in Z is at least 90%.

[61] In another aspect, the present invention provides compounds of formula $Ic_1$, or pharmaceutically acceptable salt thereof, wherein the abundance of deuterium in Z is at least 95%.

[62] In another aspect, the present invention provides compound of formula $Id_1$ or pharmaceutically acceptable salt thereof:

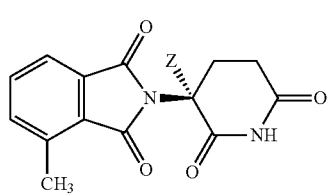

$Id_1$ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

[63] In another aspect, the present invention provides compounds of formula $Id_1$, or pharmaceutically acceptable salt thereof, wherein the abundance of deuterium in Z is at least 80%.

[64] In another aspect, the present invention provides compounds of formula $Id_1$, or pharmaceutically acceptable salt thereof, wherein the abundance of deuterium in Z is at least 90%.

[65] In another aspect, the present invention provides compounds of formula $Id_1$, or pharmaceutically acceptable salt thereof, wherein the abundance of deuterium in Z is at least 95%.

Unless indicated otherwise, when a D is specifically recited at a position or is shown in a formula, this D represents a mixture of hydrogen and deuterium where the amount of deuterium is about 100% (i.e., the abundance of deuterium is from 90% to 100%). In certain aspects, the abundance of deuterium is from 97% to 100%).

The 3'-deuterium group shown in formula I (i.e., Z) means that the compound of formula I has been isotopically enriched at the 3' position and is different and distinct from the corresponding non-enriched compound.

Compound refers to a quantity of molecules (a molecule of compound (a) of formula II being the group of atoms having the above structure and defined as $C_{18}H_{16}DN_3O_5$) that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

In another aspect, the stereoisomeric purity of the compound of the present invention (the % excess by weight of the shown stereoisomer versus the not shown stereoisomer in the compound) is independently at least 33% (i.e., 66% desired isomer versus 33% undesired isomer). Additional examples of the stereoisomeric purity of the compound of formula Ia include, but are not limited to, at least 40, 45, 50, 55, 60, 65, 70, 75, 80%, 85%, 90%, 95%, to 100% by weight.

The present invention is based on stabilizing 2-(2',6'-dioxo-3'-deutero-piperidin-3'-yl)isoindoles via deuteration at the 3' position. The C-D bond at the 3'-position is stronger than the naturally occurring C—H bond. The 3'-deuterium is expected to slow the racemization of the stereogenic center at the 3' position.

With hydrogen atoms being present in formulae I-$IIb_1$, the 2-(2',6'-dioxo-3'-deutero-piperidin-3'-yl)isoindoles of the present invention can be enriched beyond the 3' position. For example, in formula II replacing one of $R^1$-$R^{12e}$ with a deuterium would result in a 6.25% enrichment (16 starting hydrogens, 1/16×100=6.25%). Thus examples of additional enrichment of the 3'-deutero-compound of formula II include, but are not limited to, 12.5 (2 additional deuteriums), 18.75, 25, 31.25, 37.5, 43.75, 50, 56.25, 62.5, 68.75, 75, 81.25, 87.5, 93.75, and 100% enrichment. In order to achieve additional enrichment less than about 6.25%, only partial deuteration of one site is required.

For other compounds of the present invention, enrichment beyond the 3' position includes the presence of at least one additional deuterium. For example, enrichment can include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, etc., up to the total number of hydrogen atoms present and depending on the number of hydrogens present.

The invention also relates to isolated or purified 2-(2',6'-dioxo-3'-deutero-piperidin-3'-yl)isoindoles. The isolated or purified 2-(2',6'-dioxo-3'-deutero-piperidin-3'-yl)isoindoles is a group of molecules (i.e., an isolated compound) whose deuterium levels are above the naturally occurring levels. The isolated or purified 2-(2',6'-dioxo-3'-deutero-piperidin-3'-yl)isoindoles can be obtained by techniques known to those of skill in the art.

Isolated means that the non-naturally occurring 2-(2',6'-dioxo-3'-deutero-piperidin-3'-yl)isoindole is purified (e.g., from the reaction solution in which it was prepared). Examples of the purity of the isolated 2-(2',6'-dioxo-3'-deutero-piperidin-3'-yl)isoindole (or indoles when there is more than one type of compound) include, but are not limited to, at least 50%, 55%, 60%, 65%, 70%, 75%, 80%, 85%, 90%, 95%, to 100% with respect to non-deuterium-enriched 2-(2', 6'-dioxo-piperidin-3'-yl)isoindole components being present.

The invention also relates to mixture of compounds, which means that more than one type of deuterated compound is being claimed (e.g., one compound wherein only some of the molecules have $R_1$=D or a compound wherein some molecules have $R_1$=D and a second set of molecules wherein $R_2$=D).

The invention also relates to compositions comprising 2-(2',6'-dioxo-3'-deutero-piperidin-3'-yl)isoindoles. The compositions require the presence of the 2-(2',6'-dioxo-3'-deutero-piperidin-3'-yl)isoindole that is greater than its natural abundance. For example, the compositions of the invention can comprise (a) a µg of a 2-(2',6'-dioxo-3'-deutero-piperidin-3'-yl)isoindole; (b) a mg; and, (c) a gram.

In another aspect, the invention provides an amount of a novel 2-(2',6'-dioxo-3'-deutero-piperidin-3'-yl)isoindole. Examples of amounts include, but are not limited to (a) at least 0.01, 0.02, 0.03, 0.04, 0.05, 0.1, 0.2, 0.3, 0.4, 0.5, to 1 mole, (b) at least 0.1 moles, and (c) at least 1 mole of the compound. The present amounts also cover lab-scale (e.g., gram scale), kilo-lab scale (e.g., kilogram scale), and industrial or commercial scale (e.g., multi-kilogram or above scale) quantities as these will be more useful in the actual manufacture of a pharmaceutical. Industrial/commercial scale refers to the amount of product that would be produced in a batch that was designed for clinical testing, formulation, sale/distribution to the public, etc.

In another aspect, the invention provides novel pharmaceutical compositions, comprising: a pharmaceutically acceptable carrier and a therapeutically effective amount of a deuterium-enriched compound of the invention.

In another aspect, the invention provides a novel method for treating multiple myeloma (including refractory or relapsed), comprising: administering to a patient in need thereof a therapeutically effective amount of a deuterium-enriched compound of the invention.

In another aspect, the invention provides a novel method for treating multiple myeloma, comprising: administering to a patient in need thereof a first and second therapeutic agent, the first therapeutic agent being a therapeutically effective amount of a deuterium-enriched compound of the invention and the second therapeutic agent being a therapeutically effective amount of an anti-myeloma agent (e.g., dexamethasome).

In another aspect, the invention provides a novel method for treating myelodysplastic syndrome, comprising: administering to a patient in need thereof a therapeutically effective amount of a deuterium-enriched compound of the invention.

In another aspect, the invention provides a novel method for treating myelodysplastic syndrome, comprising: administering to a patient in need thereof a first and second therapeutic agent, the first therapeutic agent being a therapeutically effective amount of a deuterium-enriched compound of the invention.

In another aspect, the invention provides a novel method for treating myelodysplastic syndrome wherein the second therapeutic agent is an anti-cancer agent (e.g., dexamethasome).

In another aspect, the invention provides a novel method for treating myelodysplastic syndrome wherein the second therapeutic agent is an agent capable of improving blood cell production.

In another aspect, the invention provides a novel method for treating myelodysplastic syndrome, wherein the second active agent is a cytokine, hematopoietic growth factor, an anti-cancer agent, an antibiotic, a proteasome inhibitor, or an immunosuppressive agent.

In another aspect, the invention provides a novel method for treating myelodysplastic syndrome, wherein the second active agent is selected from etanercept, imatinib, anti-TNF-α antibodies, infliximab, G-CSF, GM-CSF, EPO, topotecan, pentoxifylline, ciprofloxacin, irinotecan, vinblastine, dexamethasone, IL2, IL8, IL18, Ara-C, vinorelbine, isotretinoin, 13-cis-retinoic acid, arsenic trioxide or a pharmacologically active mutant or derivative thereof.

In another aspect, the invention provides a novel method for treating myelodysplastic syndrome, wherein the myelodysplastic syndrome is selected from refractory anemia, refractory anemia with ringed sideroblasts, refractory anemia with excess blasts, refractory anemia with excess blasts in transformation, and chronic myelomonocytic leukemia.

In another aspect, the invention provides a novel method for treating myelodysplastic syndrome, wherein the compound of the present invention is administered before, during or after transplanting umbilical cord blood, placental blood, peripheral blood stem cell, hematopoietic stem cell preparation or bone marrow in the patient.

In another aspect, the invention provides a novel method for treating myelodysplastic syndrome, wherein the patient is not previously treated for a myelodysplastic syndrome.

In another aspect, the invention provides a novel method for treating myelodysplastic syndrome, wherein the patient has been previously treated for a myelodysplastic syndrome.

In another aspect, the invention provides an amount of a deuterium-enriched compound of the invention as described above for use in therapy.

In another aspect, the invention provides the use of an amount of a deuterium-enriched compound of the invention for the manufacture of a medicament (e.g., for the treatment of myelodysplastic syndrome).

In another aspect, the invention provides methods of treating and/or managing various diseases or disorders using a compound provided herein, or stereoisomer or pharmaceutically acceptable salt thereof.

In another aspect, the invention provides also covers solvates (e.g., hydrate) and clathrates of compounds of the present invention.

Examples of diseases or disorders include, but are not limited to, cancer, disorders associated with angiogenesis, pain including, but not limited to, Complex Regional Pain Syndrome ("CRPS"), Macular Degeneration ("MD") and related syndromes, skin diseases, pulmonary disorders, asbestos-related disorders, parasitic diseases, immunodeficiency disorders, CNS disorders, CNS injury, atherosclerosis and related disorders, dysfunctional sleep and related disorders, hemoglobinopathy and related disorders (e.g., anemia), TNFα related disorders, and other various diseases and disorders.

Examples of cancer and precancerous conditions include, but are not limited to, those described in U.S. Pat. Nos. 6,281,230 and 5,635,517 to Muller et al., in various U.S. patent publications to Zeldis, including publication nos. 2004/0220144A1, published Nov. 4, 2004 (Treatment of Myelodysplastic Syndrome); 2004/0029832A1, published Feb. 12, 2004 (Treatment of Various Types of Cancer); and 2004/0087546, published May 6, 2004 (Treatment of Myeloproliferative Diseases). Examples also include those described in WO 2004/103274, published Dec. 2, 2004. All of these references are incorporated herein in their entireties by reference.

Specific examples of cancer include, but are not limited to, cancers of the skin, such as melanoma; lymph node; breast; cervix; uterus; gastrointestinal tract; lung; ovary; prostate; colon; rectum; mouth; brain; head and neck; throat; testes; kidney; pancreas; bone; spleen; liver; bladder; larynx; nasal passages; and AIDS-related cancers. The compounds are also useful for treating cancers of the blood and bone marrow, such as multiple myeloma and acute and chronic leukemias, for example, lymphoblastic, myelogenous, lymphocytic, and myelocytic leukemias. The compounds provided herein can be used for treating and/or managing either primary or metastatic tumors.

Other specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblasts leukemia, chronic lymphocytic leukemia (CLL), Hodgkin's lymphoma, non-Hodgkin's lymphoma, cutaneous T-Cell lymphoma, cutaneous B-Cell lymphoma, diffuse large B-Cell lymphoma, low grade follicular lymphoma, metastatic melanoma (localized melanoma, including, but not limited to, ocular melanoma), malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In another aspect, the cancer is metastatic. In another aspect, the cancer is refractory or resistance to chemotherapy or radiation.

In another aspect, the invention provides methods of treating and/or managing various forms of leukemias such as chronic lymphocytic leukemia, chronic myelocytic leukemia, acute lymphoblastic leukemia, acute myelogenous leukemia and acute myeloblasts leukemia, including leukemias that are relapsed, refractory or resistant, as disclosed in U.S. publication no. 2006/0030594, published Feb. 9, 2006, which is incorporated in its entirety by reference.

The term "leukemia" refers malignant neoplasms of the blood-forming tissues. The leukemia includes, but is not limited to, chronic lymphocytic leukemia, chronic myelocytic leukemia, acute lymphoblastic leukemia, acute myelogenous leukemia and acute myeloblasts leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

In another aspect, the invention provides methods of treating and/or managing various types of lymphomas, including Non-Hodgkin's lymphoma (NHL). The term "lymphoma" refers a heterogenous group of neoplasms arising in the reticuloendothelial and lymphatic systems. "NHL" refers to malignant monoclonal proliferation of lymphoid cells in sites of the immune system, including lymph nodes, bone marrow, spleen, liver and gastrointestinal tract. Examples of NHL include, but are not limited to, mantle cell lymphoma (MCL), lymphocytic lymphoma of intermediate differentiation, intermediate lymphocytic lymphoma (ILL), diffuse poorly differentiated lymphocytic lymphoma (PDL), centrocy e lymphoma, diffuse small-cleaved cell lymphoma (DSCCL), follicular lymphoma, and any type of the mantle cell lymphomas that can be seen under the microscope (nodular, diffuse, blastic and mentle zone lymphoma).

Examples of diseases and disorders associated with, or characterized by, undesired angiogenesis include, but are not limited to, inflammatory diseases, autoimmune diseases, viral diseases, genetic diseases, allergic diseases, bacterial diseases, ocular neovascular diseases, choroidal neovascular diseases, retina neovascular diseases, and rubeosis (neovascularization of the angle). Specific examples of the diseases and disorders associated with, or characterized by, undesired angiogenesis include, but are not limited to, arthritis, endometriosis, Crohn's disease, heart failure, advanced heart failure, renal impairment, endotoxemia, toxic shock syndrome, osteoarthritis, retrovirus replication, wasting, meningitis, silica-induced fibrosis, asbestos-induced fibrosis, veterinary disorder, malignancy-associated hypercalcemia, stroke, circulatory shock, periodontitis, gingivitis, macrocytic anemia, refractory anemia, and 5q-deletion syndrome.

Examples of pain include, but are not limited to those described in U.S. patent publication no. 2005/0203142, published Sep. 15, 2005, which is incorporated herein by reference. Specific types of pain include, but are not limited to, nociceptive pain, neuropathic pain, mixed pain of nociceptive and neuropathic pain, visceral pain, migraine, headache and post-operative pain.

Examples of nociceptive pain include, but are not limited to, pain associated with chemical or thermal burns, cuts of the skin, contusions of the skin, osteoarthritis, rheumatoid arthritis, tendonitis, and myofascial pain.

Examples of neuropathic pain include, but are not limited to, CRPS type I, CRPS type II, reflex sympathetic dystrophy (RSD), reflex neurovascular dystrophy, reflex dystrophy, sympathetically maintained pain syndrome, causalgia, Sudeck atrophy of bone, algoneurodystrophy, shoulder hand syndrome, post-traumatic dystrophy, trigeminal neuralgia, post herpetic neuralgia, cancer related pain, phantom limb pain, fibromyalgia, chronic fatigue syndrome, spinal cord injury pain, central post-stroke pain, radiculopathy, diabetic neuropathy, post-stroke pain, luetic neuropathy, and other painful neuropathic conditions such as those induced by drugs such as vincristine and velcade.

As used herein, the terms "complex regional pain syndrome," "CRPS" and "CRPS and related syndromes" mean a chronic pain disorder characterized by one or more of the following: pain, whether spontaneous or evoked, including allodynia (painful response to a stimulus that is not usually painful) and hyperalgesia (exaggerated response to a stimulus that is usually only mildly painful); pain that is disproportionate to the inciting event (e.g., years of severe pain after an ankle sprain); regional pain that is not limited to a single peripheral nerve distribution; and autonomic dysregulation (e.g., edema, alteration in blood flow and hyperhidrosis) associated with trophic skin changes (hair and nail growth abnormalities and cutaneous ulceration).

Examples of MD and related syndromes include, but are not limited to, those described in U.S. patent publication no. 2004/0091455, published May 13, 2004, which is incorporated herein by reference. Specific examples include, but are not limited to, atrophic (dry) MD, exudative (wet) MD, age-related maculopathy (ARM), choroidal neovascularization (CNVM), retinal pigment epithelium detachment (PED and atrophy of retinal pigment epithelium (RPE).

Examples of skin diseases include, but are not limited to, those described in U.S. publication no. 2005/0214328A1, published Sep. 29, 2005, which is incorporated herein by reference. Specific examples include, but are not limited to, keratoses and related symptoms, skin diseases or disorders characterized with overgrowths of the epidermis, acne, and wrinkles.

As used herein, the term "keratosis" refers to any lesion on the epidermis marked by the presence of circumscribed overgrowths of the horny layer, including but not limited to actinic keratosis, seborrheic keratosis, keratoacanthoma, keratosis follicularis (Darier disease), inverted follicular keratosis, palmoplantar keratoderma (PPK, keratosis palmaris et plantaris), keratosis pilaris, and stucco keratosis. The term "actinic keratosis" also refers to senile keratosis, keratosis senilis, verruca senilis, plana senilis, solar keratosis, keratoderma or keratoma. The term "seborrheic keratosis" also refers to seborrheic wart, senile wart, or basal cell papilloma. Keratosis is characterized by one or more of the following symptoms: rough appearing, scaly, erythematous papules, plaques, spicules or nodules on exposed surfaces (e.g., face, hands, ears, neck, legs and thorax), excrescences of keratin referred to as cutaneous horns, hyperkeratosis, telangiectasias, elastosis, pigmented lentigines, acanthosis, parakeratosis, dyskeratoses, papillomatosis, hyperpigmentation of the basal cells, cellular atypia, mitotic figures, abnormal cell-cell adhesion, dense inflammatory infiltrates and small prevalence of squamous cell carcinomas.

Examples of skin diseases or disorders characterized with overgrowths of the epidermis include, but are not limited to, any conditions, diseases or disorders marked by the presence of overgrowths of the epidermis, including but not limited to, infections associated with papilloma virus, arsenical keratoses, sign of Leser-Trelat, warty dyskeratoma (WD), trichostasis spinulosa (TS), erythrokeratodermia variabilis (EKV), ichthyosis fetalis (harlequin ichthyosis), knuckle pads, cutaneous melanoacanthoma, porokeratosis, psoriasis, squamous cell carcinoma, confluent and reticulated papillomatosis (CRP), acrochordons, cutaneous horn, cowden disease (multiple hamartoma syndrome), dermatosis papulosa nigra (DPN), epidermal nevus syndrome (ENS), ichthyosis vulgaris, molluscum contagiosum, prurigo nodularis, and acanthosis nigricans (AN).

Examples of pulmonary disorders include, but are not limited to, tho described in U.S. publication no. 2005/0239842A1, published Oct. 27, 2005, which is incorporated herein by reference. Specific examples include pulmonary hypertension and related disorders. Examples of pulmonary hypertension and related disorders include, but are not limited to: primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vasular disease, congenital heart disease, HIV virus infection, drugs and toxins such as fenfluramines, congenital heart disease, pulmonary venous hypertension, chronic obstructive pulmonary disease, interstitial lung disease, sleep-disordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus including systemic and cutaneous lupus, schistosomiasis, sarcoidosis or pulmonary capillary hemangiomatosis.

Examples of asbestos-related disorders include, but not limited to, those described in U.S. publication no. 2005/0100529, published May 12, 2005, which is incorporated herein by reference. Specific examples include, but are not limited to, mesothelioma, asbestosis, malignant pleural effusion, benign exudative effusion, pleural plaques, pleural calcification, diffuse pleural thickening, rounded atelectasis, fibrotic masses, and lung cancer.

Examples of parasitic diseases include, but are not limited to, those described in U.S. publication no. 2006/0154880, published Jul. 13, 2006, which is incorporated herein by reference. Parasitic diseases include diseases and disorders caused by human intracellular parasites such as, but not limited to, *P. falcifarium, P. ovale, P. vivax, P. malariae, L. donovari, L. infantum, L. aethiopica, L. major, L. tropica, L. mexicana, L. braziliensis, T. Gondii, B. microti, B. divergens, B. coli, C. parvum, C. cayetanensis, E. histolytica, I. belli, S. mansonii, S. haematobium, Trypanosoma* ssp., *Toxoplasma* ssp., and *O. volvulus*. Other diseases and disorders caused by non-human intracellular parasites such as, but not limited to, *Babesia bovu Babesia canis, Banesia Gibsoni, Besnoitia darlingi, Cytauxzoonfelis, Eimeria* ssp., *Hammondia* ssp., and *Theileria* ssp., are also encompassed. Specific examples include, but are not limited to, malaria, babesiosis, trypanosomiasis, leishmaniasis, toxoplasmosis, meningoencephalitis, keratitis, amebiasis, giardiasis, cryptosporidiosis, isosporiasis, cyclosporiasis, microsporidiosis, *ascariasis*, trichuriasis, ancylostomiasis, strongyloidiasis, toxocariasis, trichinosis, lymphatic filariasis, onchocerciasis, filariasis, schistosomiasis, and dermatitis caused by animal schistosomes.

Examples of immunodeficiency disorders include, but are not limited to, those described in U.S. publication no. 2006/0188475, published Aug. 24, 2006. Specific examples include, but not limited to, adenosine deaminase deficiency, antibody deficiency with normal or elevated Igs, ataxia-tenlangiectasia, bare lymphocyte syndrome, common variable immunodeficiency, Ig deficiency with hyper-IgM, Ig heavy chain deletions, IgA deficiency, immunodeficiency with thymoma, reticular dysgenesis, Nezelof syndrome, selective IgG subclass deficiency, transient hypogammaglobulinemia of infancy, Wistcott-Aldrich syndrome, X-linked agammaglobulinemia, X-linked severe combined immunodeficiency.

Examples of CNS disorders include, but are not limited to, those described in U.S. publication no. 2005/0143344, published Jun. 30, 2005, which is incorporated herein by reference. Specific examples include, but are not limited to, include, but are not limited to, Amyotrophic Lateral Sclerosis, Alzheimer Disease, Parkinson Disease, Huntington's Disease, Multiple Sclerosis other neuroimmunological disorders such as Tourette Syndrome, delerium, or disturbances in consciousness that occur over a short period of time, and amnestic disorder, or discreet memory impairments that occur in the absence of other central nervous system impairments.

Examples of CNS injuries and related syndromes include, but are not limited to, those described in U.S. publication no. 2006/0122228, published Jun. 8, 2006, which is incorporated herein by reference. Specific examples include, but are not limited to, CNS injury/damage and related syndromes, include, but are not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional lability, sleep disturbances, irritability, inability to concentrate, nervousness, behavioral impairment, cognitive deficit, and seizure.

Other disease or disorders include, but not limited to, viral, genetic, allergic, and autoimmune diseases. Specific examples include, but not limited to, HIV, hepatitis, adult respiratory distress syndrome, bone resorption diseases, chronic pulmonary inflammatory diseases, dermatitis, cystic fibrosis, septic shock, sepsis, endotoxic shock, hemodynamic shock, sepsis syndrome, post ischemic reperfusion injury, meningitis, psoriasis, fibrotic disease, cachexia, graft versus host disease, graft rejection, auto-immune disease, rheumatoid spondylitis, Crohn's disease, ulcerative colitis, inflammatory-bowel disease, multiple sclerosis, systemic lupus erythrematosus, ENL in leprosy, radiation damage, cancer, asthma, or hyperoxic alveolar injury.

Examples of atherosclerosis and related conditions include, but are not limited to, those disclosed in U.S. publication no. 2002/0054899, published May 9, 2002, which is incorporated herein by reference. Specific examples include, but are not limited to, all forms of conditions involving atherosclerosis, including restenosis after vascular intervention such as angioplasty, stenting, atherectomy and grafting. All forms of vascular intervention are contemplated herein, including diseases of the cardiovascular and renal system, such as, but not limited to, renal angioplasty, percutaneous coronary intervention (PCI), percutaneous transluminal coronary angioplasty (PTCA), carotid percutaneous transluminal angioplasty (PTA), coronary bypass grafting, angioplasty with stent implantation, peripheral percutaneous transluminal intervention of the iliac, femoral or popliteal arteries, and surgical intervention using impregnated artificial grafts. The following chart provides a listing of the major systemic arteries that may be in need of treatment, all of which are contemplated herein:

Examples of dysfunctional sleep and related syndromes include, but are not limited to, those disclosed in U.S. publication no. 2005/0222209A1, published Oct. 6, 2005, which is incorporated herein by reference. Specific examples inclui but are not limited to, snoring, sleep apnea, insomnia, narcolepsy, restless leg syndrome, sleep tenors, sleep walking sleep eating, and dysfunctional sleep associated with chronic neurological or inflammatory conditions. Chronic neurological or inflammatory conditions, include, but are not limited to, Complex Regional Pain Syndrome, chronic low back pain, musculoskeletal pain, arthritis, radiculopathy, pain associated with cancer, fibromyalgia, chronic fatigue syndrome, visceral pain, bladder pain, chronic pancreatitis, neuropathies (diabetic, post-herpetic, traumatic or inflammatory), and neurodegenerative disorders such as Parkinson's Disease, Alzheimer's Disease, amyotrophic lateral sclerosis, multiple sclerosis, Huntington's Disease, bradykinesia; muscle rigidity; parkinsonian tremor; parkinsonian gait; motion freezing; depression; defective long-term memory, Rubinstein-Taybi syndrome (RTS); dementia; postural instability; hypokinetic disorders; synuclein disorders; multiple system atrophies; striatonigral degeneration; olivopontocerebellar atrophy; Shy-Drager syndrome; motor neuron disease with parkinsonian features; Lewy body dementia; Tau pathology disorders; progressive supranuclear palsy; corticobasal degeneration; frontotemporal dementia; amyloid pathology disorders; mild cognitive impairment; Alzheimer disease with parkinsonism; Wilson disease; Hallervorden-Spatz disease; Chediak-Hagashi disease; SCA-3 spinocerebellar ataxia; X-linked dystonia parkinsonism; prion disease; hyperkinetic disorders; chorea; ballismus; dystonia tremors; Amyotrophic Lateral Sclerosis (ALS); CNS trauma and myoclonus.

Examples of hemoglobinopathy and related disorders include, but are not limited to, those described in U.S. publication no. 2005/0143420A1, published Jun. 30, 2005, which is incorporated herein by reference. Specific examples include, but are not limited to, hemoglobinopathy, sickle cell anemia, and any other disorders related to the differentiation of CD34+ cells.

Examples of TNFα related disorders include, but are not limited to, those described in WO 98/03502 and WO 98/54170, both of which are incorporated herein in their entireties by reference. Specific examples include, but are not limited to: endotoxemia or toxic shock syndrome; cachexia; adult respiratory distress syndrome; bone resorption diseases such as arthritis; hypercalcemia; Graft versus Host Reaction; cerebral malaria; inflammation; tumor growth; chronic pulmonary inflammatory diseases; reperfusion injury; myocardial infarction; stroke; circulatory shock; rheumatoid arthritis; Crohn's disease; HIV infection and AIDS; other disorders such as rheumatoid arthritis, rheumatoid spondylitis, osteoarthritis, psoriatic arthritis and oth<arthritic conditions, septic shock, septis, endotoxic shock, graft versus host disease, wasting, Crohn's disease, ulcerative colitis, multiple sclerosis, systemic lupus erythromatosis, ENL in leprosy, HIV, AIDS, and opportunistic infections in AIDS; disorders such as septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, oncogenic or cancerous conditions, asthma, autoimmune disease, radiation damages, and hyperoxic alveolar injury; viral infections, such as those caused by the herpes viruses; viral conjunctivitis; or atopic dermatitis.

In another aspect, the invention provides various immunological applications, in particular, as vaccine adjuvants, particularly anticancer vaccine adjuvants, as disclosed in U.S. publication no. 2007/0048327, published Mar. 1, 2007, which is incorporated herein in its entirety by reference, is also encompassed. These aspects also relate to the uses of compounds provided herein in combination with vaccines to treat or prevent cancer or infectious diseases, and other various uses of immunomodulatory compounds such as reduction or desensitization of allergic reactions.

A compound provided herein, or stereoisomer or pharmaceutically acceptable salt thereof, can be combined with other pharmacologically active compounds ("second active agents") in methods and compositions provided herein. Certain combinations may work synergistically in the treatment of particular types diseases or disorders, and conditions and symptoms associated with such diseases or disorders. A compound provided herein, or stereoisomer or pharmaceutically acceptable salt thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetylyase inhibitors (such as, for example, SAHA and LAQ 824); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransrerase inhibitors; IkB kinase inhibitors; p38MAPK inhibitors; EGFR inhibitors (such as, for example, gefitinib and erlotinib HCL); HER-2 antibodies (such as, for example, trastuzumab (Herceptin®) and pertuzumab (Omnitarg™)); VEGFR antibodies (such as, for example, bevacizumab (Avastin™)); VEGFR inhibitors (such as, for example, flk-1 specific kinase inhibitors, SU5416 and ptk787/zk222584); P13K inhibitors (such as, for example, wortmannin); C-Met inhibitors (such as, for example, PHA-665752); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, anticancer agents and antibiotics (e.g., clarithromycin).

Specific second active compounds that can be combined with compounds provided herein vary depending on the specific indication to be treated and/or managed.

For instance, for the treatment and/or management of cancer, second active agents include, but are not limited to: semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; lenalidomide (Revlimid®); letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; pomalidomide (Actimid®); porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegatur; teloxantrone hydrochloride; temoporfin; teniposide; teroxirone; testolactone; thalidomide (Thalidomid®); thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epπsteπde; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte α interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense^; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasom<inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in mutiple myeloma cells (such as, for example, TRAIL), statins, semaxanib, cyclosporin, etanercept, doxycycline, bortezomib (Velcade®), lenalidomide (Revlimid®); pomalidomide (Actimid®); thalidomide (Thalidomid®); oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon α, pegylated interferon α (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Examples of second active agents that may be used for the treatment and/or management of pain include, but are not limited to, conventional therapeutics used to treat and/or prevent pain such as antidepressants, anticonvulsants, antihypertensives, anxiolytics, calcium channel blockers, muscle relaxants, non-narcotic analgesics, opioid analgesics, antiinflammatories, cox-2 inhibitors, immunomodulatory agents, α-adrenergic receptor agonists or antagonists, immunosuppressive agents, corticosteroids, hyperbaric oxygen, ketamine, other anesthetic agents, NMDA antagonists, and other therapeutics found, for example, in the Physician's Desk Reference 2003. Specific examples include, but are not limited to, salicylic acid acetate (Aspirin®), celecoxib (Celebrex®), Enbrel®, ketamine, gabapentin (Neurontin®), phenyloin (Dilantin®), carbamazepine (Tegretol®), oxcarbazepine (Trileptal®), valproic acid (Depakene), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), naproxen, nefazodone (Serzone®), venlafaxine (Effexor®), trazodone (Desyrel®), bupropion (Wellbutrin®), mexiletine, nifedipine, propranolol, tramadol, lamotrigine, vioxx, ziconotide, ketamine, dextromethorphan, benzodiazepines, baclofen, tizanidine and phenoxybenzamine.

Examples of second active agents that may be used for the treatment and/or management of macular degeneration and related syndromes include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an antiinflammatory compound or an antiangiogenesis compound, or a combination thereof. Specific examples include, but are not limited to, verteporfin, purlytin, an angiostatic steroid, rhuFab, interferon-2α, pentoxifylline, tin etiopurpurin, motexafin, lucentis, lutetium, 9-fluoro-11,21-dihydroxy-16, 17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-0-MaI genistin, 6'-0-Ac genistin, daidzein, daidzin, 6'-0-MaI daidzin, 6'-0-Ac daidzin, glycitein, glycitin, 6'-0-MaI glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE1O1 (Eyetech Pharmaceuticals), LY333531 (Eli Lilly), Miravant, and RETISERT implant (Bausch & Lomb). All of the references cited herein are incorporated in their entireties by reference.

Examples of second active agents that may be used for the treatment and/or management of skin diseases include, but are not limited to, keratolytics, retinoids, α-hydroxy acids, antibiotics, collagen, botulinum toxin, interferon, steroids, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of second active agents that may be used for the treatment and/or management of pulmonary hepertension and related disorders include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfari (Coumadin®), a diuretic, a cardiac glycoside, digoxin-oxygen, diltiazem, nifedipine, a vasodilator such as prostacyclin (e.g., prostaglandin 12 (PGI2), epoprostenol (EPO, Floran®), treprostinil (Remodulin®), nitric oxide (NO), bosentan (Tracleer®), amlodipine, epoprostenol (Florae), treprostinil (Remodulie), prostacyclin, tadalafil (Clalis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of second active agents that may be used for the treatment and/or management of asbestos-related disorders include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil), paclitaxel, ganciclovir, adriamycin, bleomycin, hyaluronidase, mitomycin C, mepacrine, thiotepa, tetracycline and gemcitabine.

Examples of second active agents that may be used for the treatment and/or management of parasitic diseases include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stibogluconate), interferon gamma, itraconazole, a combination of dead promastigotes and BCG, leucovorin, corticosteroids, sulfonamide, spiramycin, IgG (serology), trimethoprim, and sulfamethoxazole.

Examples of second active agents that may be used for the treatment and/or management of immunodeficiency disorders include, but are not limited to: antibiotics (therapeutic or prophylactic) such as, but not limited to, ampicillin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologies such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-α), antibodies (e.g., anti-CD40 and IgM), oligonucleotides containing unmethylated CpG motifs, and vaccines (e.g., viral and tumor peptide vaccines).

Examples of second active agents that may be used for the treatment and/or management of CNS disorders include, but are not limited to: opioids; a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment and/or management of CNS injuries and related syndromes include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids {e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, l-erythro-methylphenidate, d-erythro-methylphenidate, dl-erythro-methylphenidate, and a mixture thereof; and a diuretic agent such as, but not limited to, mannitol, furosemide, glycerol, and urea.

Examples of second active agent that may be used for the treatment and/or management of dysfunctional sleep and related syndromes include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOF cocaine, α-methyltyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbiprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of second active agents that may be used for the treatment and/or management of hemoglobinopathy and related disorders include, but are not limited to: interleukins, such as IL-2 (including recombinant IL-II ("rIL2") and canarypox IL-2), IL-IO, IL-12, and IL-18; interferons, such as interferon alfa-2a, interferon alfa-2b, interferon alfa-nl, interferon alfa-n3, interferon beta-I a, and interferon gamma-I b; and G-CSF; hydroxyurea; butyrates or butyrate derivatives; nitrous oxide; hydroxy urea; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substii such as Hemospan™ or Hemospan™ PS (Sangart).

Administration of a compound provided herein, or stereoisomer or pharmaceutically acceptable salt thereof, and the second active agents to a patient in need thereof can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One of administration for compounds provided herein is oral. Routes of administration for the second active agents or ingredients are known to those of ordinary skill in the art. See, e.g., Physicians' Desk Reference ($60^{th}$ ed., 2006).

In another aspect, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of compounds provided herein and any optional additional active agents concurrently administered to the patient.

As discussed elsewhere herein, also encompassed is a method of reducing, treating and/or managing adverse or undesired effects associated with conventional therapy including, but not limited to, surgery, chemotherapy, radiation therapy, hormonal therapy, biological therapy and immunotherapy. Compounds provided herein and other active ingredients can be administered to a patient prior to, during, or after the occurrence of the adverse effect associated with conventional therapy.

In another aspect, the prophylactic or therapeutic agents provided herein can be cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in another aspect, a compound provided herein is administered daily in a single or divided doses in a four to six week cycle with a rest period of about a week or two weeks. Cycling therapy further allows the frequency, number, and length of dosing cycles to be increased. Thus, another aspect encompasses the administration of a compound provided herein for more cycles than are typical when it is administered alone. In another aspect, a compound provided herein is administered for a greater number of cycles than would typically cause dose-limiting toxicity in a patient to whom a second active ingredient is not also being administered.

In another aspect, a compound provided herein is administered in a cycle of about 16 weeks, about once or twice every day. One cycle can comprise the administration of the compound and at least one (1) or three (3) weeks of rest. Examples of the number of cycles administered include (a) from about 1 to about 12 cycles, (b) from about 2 to about 10 cycles, and (c) from about 2 to about 8 cycles.

In another aspect, a compound provided herein is administered daily and continuously for three or four weeks at a dose of from about 0.1 mg to about 500 mg per day, followed by a rest of one or two weeks. In other aspects, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In another aspect, a compound provided herein and a second active ingredient are administered orally, with administration of the compound provided herein occurring 30 to 60 minutes prior to the second active ingredient, during a cycle of four to six weeks. In another aspect, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

In another aspect, the invention provides methods for up-regulating the levels of CD59. In certain embodiments, the levels of CD59 are up-regulated by stimulating gene expression (e.g., transcription and translation). In certain aspects, the levels of CD59 are up-regulated by more than about 10%, 20%, 30%, 40%, 50%, 60%, 70%, 80%, 90% or more as determined by methods known in the art as well as those described herein. Further provided are methods of treating, preventing or managing diseases associated with CD59 deficiency, including hematologic diseases, such as, for example, paroxysmal nocturnal hemoglobinuria (PNH).

In another aspect, the invention provides methods of treating and/or managing ischemic-reperfusion injury. Ischemia-reperfusion injury (IRI) is the primary cause of acute renal failure and is a predominant cause of tissue damage in conditions such as stroke, myocardial infarction, cardiopulmonary bypass, and intestinal ischemia. The role of the complement system as an important mediator of renal IRI has been demonstrated in numerous animal studies. CD59 deficient mice display upregulation of membrane attack complex and considerably more sensitive to IRI. In certain embodiments, the methods of treating, preventing or managing ischemic-reperfusion injury by upregulating the levels of CD59 are provided.

In another aspect, the present invention provides methods of treating and/or managing autoimmune hemolytic anemia. Without being limited by a particular theory, it is believed that autoimmune hemolytic anemia (AIHA) can result from complement-mediated lysis by autoantibodies and is found in some patients secondary to systemic lupus erythematosus (SLE). Studies comparing CD59 levels in red blood cells of SLE patients with and without secondary AIHA to patients with primary AIHA or normal volunteers have shown a decrease in CD59 in SLE plus AIHA patients but not in the other patient groups. In certain embodiments, provided herein are methods of treating, preventing or managing autoimmune hemolytic anemia by upregulating the levels of CD59.

In another aspect, the present invention provides methods of treating preventing or managing autoimmune disease, such as lupus erythematosis and rheumatoid arthritis are provided.

In another aspect, the present invention provides methods of treating one or more symptoms associated with PNH and other hemolytic diseases provided herein. Such symptoms include, for example, abdominal pain, fatigue, dyspnea and insomnia. Without being limited by a particular theory, symptoms can be the direct result of lysis of red blood cells (e.g., hemoglobinuria, anemia, fatigue, low red blood cell count, etc.) or the symptoms can result from low nitric oxide (NO) levels in the patient's bloodstream (e.g., abdominal pain, erectile dysfunction, dysphagia, thrombosis, etc.). It has recently been reported that almost all patients with greater than 40% PNH type III granulocyte clone have thrombosis, abdominal pain, erectile dysfunction and dysphagia, indicating a high hemolytic rate (see, Moyo et al., *British J. Haematol.* 126:133-138 (2004)).

In another aspect, the present invention provides treating and/or managing hemolytic diseases including symptoms such as hemoglobinuria, anemia, hemoglobinemia, dysphagia, fatigue, erectile dysfunction, recurrent abdominal pain and thrombosis associated with paroxysmal nocturnal hemoglobinuria. In certain embodiment, provided herein are methods of treating hemolysis associated with paroxysmal nocturnal hemoglobinuria in a patient afflicted with a hemolytic disease. In certain embodiments, treating hemolysis means that the duration of time a person suffers from hemolysis is reduced by about 5%, 10%, 15%, 20%, 25%, 30%, 35%, 40%, 50% or more using any method known in the art. In certain embodiments, treating hemolysis means that the intensity of hemolysis is reduced by about 5%, 10%, 15%, 20%, 25%, 30%, 35%, 40%, 50% or more using any method known in the art.

In certain aspects, treating hemoglobinuria means a reduction in the number of times a person has red, brown, or darker urine, wherein the reduction is typically about 5%, 10%, 15%, 20%, 25%, 30%, 35%, 40%, 50% or more as determined by any method known in the art. Hemoglobinuria is a symptom resulting from the inability of a patient's natural levels of haptoglobin to process all the free hemoglobin released into the bloodstream as a result of intravascular hemolysis. Without being bound by any particular theory, it is believed that by reducing the lysis of red blood cells, the methods provided herein reduce the amount of free hemoglobin in the bloodstream and urine thereby treating hemoglobinuria.

In another aspect, the present invention provides a method of treating fatigue associated with paroxysmal nocturnal hemoglobinuria and other hemolytic diseases. In an aspect, treating fatigue means the duration of time a person suffers from fatigue is reduced by about 5%, 10%, 15%, 20%, 25%, 30%, 35%, 40%, 50% or more as determined by any method known in the art. In one aspect, treating fatigue means the intensity of fatigue is reduced by about 5%, 10%, 15%, 20%, 25%, 30%, 35%, 40%, 50% or more as determined by any method known in the art. Without being bound by any particular theory, it is believed that fatigue is a symptom associated with intravascular hemolysis, as the fatigue relents when hemoglobinuria resolves even in the presence of anemia. In an aspect, the methods provided herein treat fatigue by reducing the lysis of red blood cells.

In another aspect, a method of treating abdominal pain associated with paroxysmal nocturnal hemoglobinuria and other hemolytic diseases is contemplated. In one aspect, treating abdominal pain means the duration of time a person suffers from abdominal pain is reduced by about 5%, 10%, 15%, 20%, 25%, 30%, 35%, 40%, 50% or more as determined by any method known in the art. In one aspect, treating abdominal pain means the intensity of abdominal pain is reduced by about 5%, 10%, 15%, 20%, 25%, 30%, 35%, 40%, 50% or more as determined by any method known in the art. Without being bound by any particular theory, it is believed that abdominal pain is a symptom resulting from the inability of a patient's natural levels of haptoglobin to process all the free hemoglobin released into the bloodstream as a result of intravascular hemolysis, resulting in the scavenging of nitric oxide (NO) and intestinal dystonia and spasms. In one aspect, the methods provided herein reduce the amount of free hemoglobin in the bloodstream, thereby reducing abdominal pain, by reducing the lysis of red blood cells.

Further provided are methods of treating dysphagia associated with paroxysmal nocturnal hemoglobinuria and other hemolytic diseases. In one aspect treating dysphagia means the duration of time a person has dysphagia attacks is reduced by about 5%, 10%, 15%, 20%, 25%, 30%, 35%, 40%, 50% or more as determined by any method known in the art. In one aspect treating dysphagia means the intensity of dysphagia attacks is reduced by about 5%, 10%, 15%, 20%, 25%, 30%, 35%, 40%, 50% or more as determined by any method known in the art. Without being bound by any particular theory, it is believed that dysphagia is a symptom resulting from the inability of a patient's natural levels of haptoglobin to process all the free hemoglobin released into the bloodstream as a result of intravascular hemolysis, resulting in the scavenging of NO and esophageal spasms. In one aspect, the methods provided herein treat dysphagia by reducing the lysis of red blood cells, thereby reducing the amount of free hemoglobin in the bloodstream.

In another aspect, the present invention provides methods of trating erectile dysfunction associated with paroxysmal nocturnal hemoglobinuria and other hemolytic diseases. Without being bound by any particular theory, it is believed that erectile dysfunction is a symptom associated with scavenging of NO by free hemoglobin released into the bloodstream as a result of intravascular hemolysis. In one aspect, methods herein reduce the amount of free hemoglobin in the bloodstream, thereby increasing serum levels of NO and treating erectile dysfunction associated with paroxysmal nocturnal hemoglobinuria.

In another aspect, a method of treating thrombosis associated with paroxysmal nocturnal hemoglobinuria and other hemolytic diseases is contemplated. Treating thrombosis means the duration of time a person has thrombosis attacks is reduced by about 5%, 10%, 15%, 20%, 25%, 30%, 35%, 40%, 50% or more as determined by any method known in the art. Treating thrombosis means the intensity of thrombosis attacks is reduced by about 5%, 10%, 15%, 20%, 25%, 30%, 35%, 40%, 50% or more as determined by any method known in the art. Without being bound by any particular theory, it is believed that thrombosis is a symptom associated with scavenging of NO by free hemoglobin released into the bloodstream as a result of intravascular hemolysis and/or the lack of CD59 on the surface of platelets resulting in terminal complement mediated activation of the platelet. By reducing the lysis of red blood cells, the methods provided herein reduce the amount of free hemoglobin in the bloodstream, thereby increasing serum levels of NO and treating thrombosis associated with paroxysmal nocturnal hemoglobinuria.

In another aspect, the present invention provides a method of treating anemia pain associated with paroxysmal nocturnal hemoglobinuria and other hemolytic diseases. In one aspect, treating amenia pain means the duration of time a person has anemia pain is reduced by about 5%, 10%, 15%, 20%, 25%, 30%, 35%, 40%, 50% or more as determined by any method known in the art. In one aspect, treating amenia pain means the intensity of anemia pain is reduced by about 5%, 10%, 15%, 20%, 25%, 30%, 35%, 40%, 50% or more as determined by any method known in the art. Without being bound by any particular theory, it is believed that anemia in hemolytic diseases results from the blood's reduced capacity to carry oxygen due to the loss of red blood cell mass. In certain embodiment, the methods provided herein assist red blood cell levels to increase by reducing the lysis of red blood cells, thereby treating anemia associated with paroxysmal nocturnal hemoglobinuria.

It has been reported in the literature that CD59 is inactivated by glycation in the presence of high concentrations of glucose or other glycating sugars, Davies et al., *Immunology*. 2005 February; 114(2):280-6. It has been further reported that glycation-induced inactivation of CD59 as a factor contributing to anaemia in type I diabetes. Therefore, provided herein are methods of treating anaemia in type I diabetes.

In another aspect, a method of increasing the proportion of complement sensitive type III red blood cells in total red blood cell content in a patient afflicted with a hemolytic disease is contemplated. In certain embodiments, the proportion of PNH type III red blood cells of the subject's total red blood cell content is increased by 5%, 10%, 15%, 20%, 25%, 30%, 35%, 40%, 50%, 75% or more as compared to that before the treatment. The proportion of PNH type III red blood cells can be determined by any method known in the art. By increasing the proportion of complement sensitive type III red blood cells, the total red blood cell count is also increased thereby treating fatigue, anemia and reducing the patient's need for blood transfusions. The reduction in transfusions can be in frequency of transfusions, amount of blood units transfused, or both.

In one aspect, provided herein are methods of increasing red blood cell count in a patient afflicted with a hemolytic disease. In other aspects, the methods increase red blood cell count in a patient afflicted with a hemolytic disease resulting in the proportion of PNH type III red blood cells of the subject's total red blood cell content to greater than 5%, 10%, 15%, 20%, 25%, 30%, 35%, 40%, 50%, 75% or more as compared to that before the treatment as determined by any method known in the art. In some embodiments, the methods provided herein decrease the frequency of transfusions in a patient suffering from a hemolytic disease, such as PNH, by about 5%, 10%, 15%, 20%, 25%, 30%, 35%, 40%, 50%, 75%, 80%, 90%, 95% or more as compared to that before the treatment as determined by any method known in the art.

In another aspect, the present invention provides methods of increasing the nitric oxide (NO) levels in a patient having PNH or some other hemolytic disease. Without being bound by any particular theory, it is believed that low NO levels arise in patients suffering from PNH or other hemolytic diseases as a result of scavenging of NO by free hemoglobin released into the bloodstream as a result of intravascular hemolysis. By reducing the lysis of red blood cells, the methods provided herein reduce the amount of free hemoglobin in the bloodstream, thereby increasing serum levels of NO. In certain embodiments, the serum levels of NO are increased by about 5%, 10%, 15%, 20%, 25%, 30%, 35%, 40%, 50%, 75%, 80%, 90%, 95% or more as determined by any method known in the art. In certain embodiments, NO homeostasis is restored as evidenced by a resolution of symptoms attributable to NO deficiencies as compared to that before the treatment.

It has been reported in the literature that deficiency of CD59 enhances T cell activity, see, Longhi et al., Trends in Immunology, (27) 2, 2006, 102-107. In certain aspects, the administration of the compounds provided herein can effectively down-regulate T cell activity.

In another aspect, the immunomodulatory compound, or a pharmaceutically acceptable salt, solvate (e.g., hydrate), stereoisomer, clathrate, or prodrug thereof, can be administered in combination with one or more second active agents, such as, and/or in combination with blood transfusions, anti-coagulation therapy, bone marrow transplantation and combinations thereof.

It is further contemplated that a combination therapy can be used wherein an immunomodulatory compound provided herein is administered in combination with a regimen of known therapy for the hemolytic disease. Such regimens include administration of 1) one or more compounds known to increase hematopoiesis (for example, either by boosting production, eliminating stem cell destruction or eliminating stem cell inhibition) in combination with 2) a compound selected from a group of compounds which bind to one or more complement components, compounds which block the generation of one or more complement components and compounds which block the activity of one or more complement components. Suitable compounds known to increase hematopoiesis include, for example, steroids, immunosuppressants (such as, cyclosporin), anti-coagulants (such as, warfarin), folic acid, iron and the like, erythropoietin (EPO), immunosuppressants such as, antithymocyte globulin (ATG) and anti-lymphocyte globulin (ALG), EPO derivatives, and darbepoetin alfa (commercially available as Aranesp® (Aranesp® is a man-made form of EPO produced in Chinese hamster ovary (CHO) cells by recombinant DNA technology)). In certain embodiment, the combination therapy includes administration of an anti-05 antibody selected from the group consisting of eculizumab, h5G 1.1-mAb, h5G1.1-scFv and other functional fragments of h5G1.1. In certain embodiment, the anti-05 antibody is eculizumab.

The combined use of the immunomodulatory compounds provided herein and conventional therapy may provide a unique treatment regimen effective in certain patients. Without being limited by theory, it is believed that immunomodulatory compounds provided herein may provide additive or synergistic effects when given concurrently with other therapy.

In one aspect, an immunomodulatory compound herein can be administered in an amount of from about 0.10 to about 150 mg, from about 1 to about 50 mg or from about 5 to about 25 mg orally and daily alone, or in combination with a second active agent disclosed herein, prior to, during, or after the use of conventional therapy.

In another aspect, the present invention provides methods of treating and/or managing a disease or disorder associated with a hypoleptinemic state.

Examples of disorders associated with a hypoleptinemic state include, but are not limited to: metabolic and eating disorders such as, but not limited to, lipodystrophy syndrome and anorexia nervosa; hypoleptinemia related neuroendocrine dysfunctions; hypoleptinemia related immunodeficiencies; hypothalamic amenorrhea; CNS disorders such as, but not limited to, acromegaly (pituitary adenoma); hypoleptinemia related infertility syndromes; skin damage; wounds; long-term hemodialysis; and loss of hair.

In another aspect, the present invention provides methods of treating or preventing myelodysplastic syndrome ("MDS") which comprise administering to a patient in need thereof a therapeutically or prophylactically effective amount of an immunomodulatory compound of the invention or a pharmaceutically acceptable salt, solvate, hydrate, stereoisomer, clathrate, or prodrug thereof. The invention also encompasses methods of managing MDS (e.g., lengthening the time of remission) which comprise administering to a patient in need of such management a therapeutically or prophylactically effective amount of an immunomodulatory compound of the invention, or a pharmaceutically acceptable salt, solvate, hydrate, stereoisomer, clathrate, or pro drug thereof.

In another aspect, the invention provides the use of one or more immunomodulatory compounds in combination with conventional therapies presently used to treat, prevent or manage MDS such as hematopoietic growth factors, cytokines, cancer chemotherapeutics, stem cell transplantation and other transplantations.

As used herein, the term "myelodysplastic syndromes" or "MDS" means hematopoietic stem cell disorders characterized by one or more of the following: ineffective blood cell production, progressive cytopenias, risk of progression to acute leukemia or cellular marrow with impaired morphology and maturation (dysmyelopoiesis). The term "myelodysplastic syndromes" or "MDS" unless otherwise noted includes: refractory anemia, refractory anemia with ringed sideroblasts, refractory anemia with excess blasts, refractory anemia with excess blasts in transformation and chronic myelomonocytic leukemia. The symptoms associated with MDS include, but are not limited to, anemia, thrombocytopenia, neutropenia, cytopenia, bicytopenia (two deficient cell lines), and pancytopenia (three deficient cell lines).

The invention may be embodied in other specific forms without departing from the spirit or essential attributes thereof. This invention encompasses all combinations of preferred aspects of the invention noted herein. It is understood that any and all aspects of the invention may be taken in conjunction with any other aspect or aspects to describe additional aspects. It is also to be understood that each individual element of the aspects is intended to be taken individually as its own independent aspect. Furthermore, any element of an aspect is meant to be combined with any and all other elements from any aspect to describe an additional aspect.

DEFINITIONS

The examples provided in the definitions section as well as the remainder of this application are non-inclusive unless otherwise stated. They include but are not limited to the recited examples.

The compounds herein described may have asymmetric centers, geometric centers (e.g., double bond), or both. All chiral, diastereomeric, racemic forms and all geometric isomeric forms of a structure are intended, unless the specific stereochemistry or isomeric form is specifically indicated. Compounds of the present invention containing an asymmetrically substituted atom may be isolated in optically active or racemic forms. It is well known in the art how to prepare optically active forms, such as by resolution of racemic forms, by synthesis from optically active starting materials, or through use of chiral auxiliaries. Geometric isomers of olefins, C=N double bonds, or other types of double bonds may be present in the compounds described herein, and all such stable isomers are included in the present invention. Specifically, cis and trans geometric isomers of the compounds of the present invention may also exist and may be isolated as a mixture of isomers or as separated isomeric forms. All processes used to prepare compounds of the present invention and intermediates made therein are considered to be part of the present invention. All tautomers of shown or described compounds are also considered to be part of the present invention.

"Alkyl" and "alkylene" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, and s-pentyl.

As noted previously, "alkyl" also includes deuterated alkyl. Each alkyl group contains 2n+1 hydrogen atoms, wherein n=the number of carbon atoms. Deuterated alkyl covers alkyls groups having from 1 to 2n+1 deuteriums. Deuterated $C_{1-6}$ alkyl, for example, includes $C_1$ ($d_{1-3}$), $C_2$ ($d_{1-5}$), $C_3$ ($d_{1-7}$), $C_4$ ($d_{1-9}$), $C_5$ ($d_{1-11}$), and $C_6$ ($d_{1-13}$), alkyl groups.

"Haloalkyl" and "haloalkylene" include alkyl groups as defined above (including deuteration), wherein one or more hydrogens are replaced by a halogen atom selected from Cl, F, Br, and I. Examples of haloalkyl include trifluoromethyl, 1,1,1-trifluoroethyl, and perfluoroethyl.

"Alkenyl" includes the specified number of hydrocarbon atoms in either straight or branched configuration with one or more unsaturated carbon-carbon bonds that may occur in any stable point along the chain, such as ethenyl and propenyl. $C_{2-6}$ alkenyl includes $C_2$, $C_3$, $C_4$, $C_5$, and $C_6$ alkenyl groups.

As noted previously, "alkenyl" also includes deuterated alkenyl. Each alkenyl group contains 2n−1 hydrogen atoms, wherein n=the number of carbon atoms. Deuterated alkenyl covers alkenyls groups having from 1 to 2n−1 deuteriums. Deuterated $C_{2-6}$ alkenyl, for example, includes $C_2$ ($d_{1-3}$), $C_3$ ($d_{1-5}$), $C_4$ ($d_{1-7}$), $C_5$ ($d_{1-6}$), and $C_6$ ($d_{1-11}$), alkenyl groups.

"Alkynyl" includes the specified number of hydrocarbon atoms in either straight or branched configuration with one or more triple carbon-carbon bonds that may occur in any stable point along the chain, such as ethynyl and propynyl. $C_{2-6}$ Alkynyl includes $C_2$, $C_3$, $C_4$, $C_5$, and $C_6$ alkynyl groups.

As noted previously, "alkynyl" also includes deuterated alkynyl. Each alkynyl group contains 2(n−2)+1 hydrogen atoms, wherein n=the number of carbon atoms. Deuterated alkenyl covers alkenyls groups having from 2(n−2)+1 deuteriums. Deuterated $C_{2-6}$ alkynyl, for example, includes $C_3$ ($d_{1-3}$), $C_4$ ($d_{1-5}$), $C_5$ ($d_{1-7}$), and $C_6$ ($d_{1-6}$), alkynyl groups.

"Cycloalkyl" includes the specified number of hydrocarbon atoms in a saturated ring, such as cyclopropyl, cyclobutyl, cyclopentyl, cyclohexyl, cycloheptyl, and cyclooctyl. $C_{3-8}$ cycloalkyl includes $C_3$, $C_4$, $C_5$, $C_6$, $C_7$, and $C_8$ cycloalkyl groups.

As noted previously, "cycloalkyl" also includes deuterated cycloalkyl. Each cycloalkyl group contains 2n−1 hydrogen atoms, wherein n=the number of carbon atoms. Deuterated cycloalkyl covers cycloalkyl groups having from 1 to 2n−1 deuteriums. Deuterated $C_{3-8}$ cycloalkyl, for example, includes $C_3$ ($d_{1-5}$), $C_4$ ($d_{1-7}$), $C_5$ ($d_{1-6}$), $C_6$ ($d_{1-11}$), $C_7$ ($d_{1-13}$), and $C_8$ ($d_{1-15}$), cycloalkyl groups.

"Aryl" refers to any stable 6, 7, 8, 9, 10, 11, 12, or 13 membered monocyclic, bicyclic, or tricyclic ring, wherein at least one ring, if more than one is present, is aromatic. Examples of aryl include fluorenyl, phenyl, naphthyl, indanyl, adamantyl, and tetrahydronaphthyl.

As noted previously, "aryl" also includes deuterated aryl. For example, phenyl includes $d_{1-6}$ phenyl.

"Heterocycloalkyl" refers to any stable monocyclic, bicyclic, or tricyclic heterocyclic ring that is non-aromatic, and which consists of the specified number of carbon atoms and 1, 2, 3, or 4 heteroatoms independently selected from the group consisting of N, O, and S. If the heterocycloalkyl group is bicyclic or tricyclic, then at least one of the two or three rings must contain a heteroatom, though both or all three may each contain one or more heteroatoms. The N group may be N, NH, or N-substituent, depending on the chosen ring and if substituents are recited. The nitrogen and sulfur heteroatoms may optionally be oxidized (e.g., S, S(O), S(O)$_2$, and N—O). The heterocycloalkyl ring may be attached to its pendant group at any heteroatom or carbon atom that results in a stable structure. A heterocycloalkyl group can have one or more carbon-carbon double bonds or carbon-heteroatom double bonds in the ring as long as the ring is not rendered aromatic by their presence. The heterocycloalkyl rings described herein may be substituted on carbon or on a nitrogen atom if the resulting compound is stable.

As noted previously, "heterocycloalkyl" also includes deuterated heterocycloalkyl. For example, piperidinyl and piperazino include $d_{1-10}$ piperidinyl or $d_{1-9}$ piperazino.

Examples of heterocycloalkyl include aziridinyl, pyrrolidinyl, pyrrolidino, piperidinyl, piperidino, piperazinyl, piperazino, morpholinyl, morpholino, thiomorpholinyl, thiomorpholino, tetrahydrofuranyl, tetrahydrothiofuranyl, tetrahydropyranyl, and pyranyl.

"Heteroaryl" refers to any stable 5, 6, 7, 8, 9, 10, 11, or 12 membered monocyclic, bicyclic, or tricyclic heterocyclic ring that is aromatic, and which consists of carbon atoms and 1, 2, 3, or 4 heteroatoms independently selected from the group consisting of N, O, and S. If the heteroaryl group is bicyclic or tricyclic, then at least one of the two or three rings must contain a heteroatom, though both or all three may each contain one or more heteroatoms. If the heteroaryl group is bicyclic or tricyclic, then only one of the rings must be aromatic. The N group may be N, NH, or N-substituent, depending on the chosen ring and if substituents are recited. The nitrogen and sulfur heteroatoms may optionally be oxidized (e.g., S, S(O), S(O)$_2$, and N—O). The heteroaryl ring may be attached to its pendant group at any heteroatom or carbon atom that results in a stable structure. The heteroaryl rings described herein may be substituted on carbon or on a nitrogen atom if the resulting compound is stable.

As noted previously, "heteroaryl" also includes deuterated heteroaryl. For example, furanyl or thienyl include $d_{1-5}$ furanyl or $d_{1-5}$ thienyl.

Examples of heteroaryl includes acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, naphthyridinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, pteridinyl, pyranyl, pyrazinyl, pyrazolyl, pyridazinyl, pyridooxazole, pyridoimidazole, pyridothiazole, pyridinyl, pyridyl, pyrimidinyl, 2H-pyrrolyl, pyrrolyl, quinazolinyl, quinolinyl, 4H-quinolizinyl, quinoxalinyl, quinuclidinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

"Host" preferably refers to a human. It also includes other mammals including the equine, porcine, bovine, feline, and canine families.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

"Therapeutically effective amount" includes an amount of a compound of the invention that is effective when administered alone or in combination to treat the desired condition or disorder. "Therapeutically effective amount" includes an amount of the combination of compounds claimed that is effective to treat the desired condition or disorder. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antiviral effect, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palimitic, pamoic, pantothenic, phenylacetic, phosphoric, polygalacturonic, propionic, salicyclic, stearic, subacetic, succinic, sulfamic, sulfanilic, sulfuric, tannic, tartaric, toluenesulfonic, and valeric. (See, for example, Berge et al. (1977) "Pharmaceutical Salts", J. Pharm. Sci. 66:1-19.)

Synthesis

The hydrogens present on the 2-(2',6'-dioxo-3'-deuteropiperidin-3'-yl)isoindoles have different capacities for exchange with deuterium. For example, hydrogen atoms $R^1$ and $R^{11}$ (if H) are exchangeable in $H_2O/D_2O$. Hydrogen atoms $R^2$-$R^3$ and the 3' deuterium can be exchanged under basic conditions. The remaining hydrogen atoms are not easily exchangeable for deuterium atoms, though some may be depending on the specific moieties selected from $R^{12-17}$. Deuterium atoms at the remaining positions may be incorporated by the use of deuterated starting materials or intermediates via the known synthetic methods for the synthesis of 2-(2',6'-dioxo-3'-deutero-piperidin-3'-yl)isoindoles as described in U.S. Pat. No. 7,091,353 (U.S '353)(e.g., see section 6 starting in Column 81), the contents of which are incorporated herein by reference. It is contemplated that the presently described deuteriated 2-(2',6'-dioxo-3'-deutero-piperidin-3'-yl)isoindoles can be prepared by incorporating deuterated starting materials into the synthetic route of U.S. '353. Alternatively, deuterium is expected to be incorporated at the exchangeable and acidic positions of the final compound (e.g., $R^1$ or the 3' position, respectively).

Scheme 1 below provides an exemplary synthetic route for preparing deuterated 2-(2',6'-dioxo-3'-deutero-piperidin-3'-yl)isoindoles.

Scheme 1

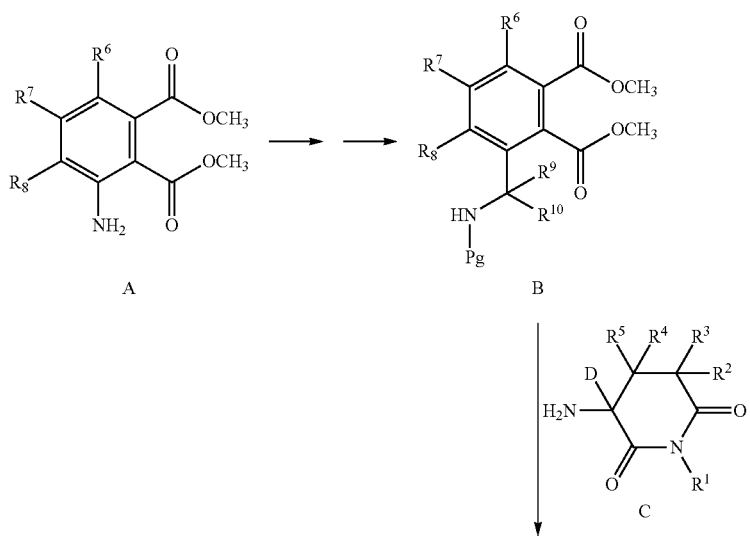

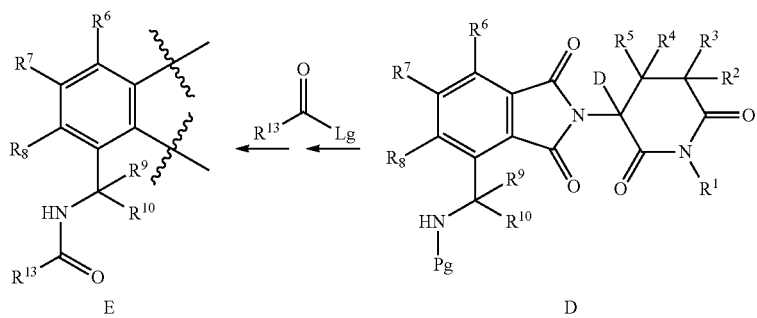

The compounds of the present invention can be obtained starting with A, which can be optionally deuterated. Compound A is formed by reducing the corresponding nitro group. The amino group of Compound A can then be chain extended via the Sandmeyer procedure to form a nitrile moiety, which can be reduced (e.g., hydrogenated in the presence of Pd/C and $H_2$ or $D_2$) to form the corresponding amine that is protected (e.g., reacting with di-t-butyl dicarbonate) resulting in Compound B. Compound C, an appropriately substituted amino-dioxo-piperidine can then be reacted, typically in the presence of a base (e.g., diisopropylethyl amine) with Compound B to form Compound D. The 3-deutero group of Compound C is optional as this deuterium is in an acidic position and can be added at a later stage using a base in $D_2O$. Compound D is then deprotected (e.g., hydrolysis of the t-butyl-carbamate group under aqueous HCl conditions) to expose the amine, which can be reacted with various groups. Reaction with an $R^{13}$—C(O)-leaving group (e.g., where the leaving group is a chloride) provides the $R^{13}$-amide of Compound E. Alternatively, the amide moiety can be formed with Compound B, prior to reaction with Compound C to form the imide.

A number of deuterated glutamines (Compound C) have previously been made including 2,3,4-trideutero-glutamine (i.e., $R_2$=D, $R_4$=D, and 3'-D is present), which was made via the deuterium reduction of 6-carboxy-3(2H)-pyridazone (see Stogniew, J. Labelled Compounds and Radiopharmaceuticals 1981, 18(6), 897-903), and 2,2,3,3,4 pentadeutero-glutamine (i.e., $R_2$-$R_5$=D and 3'-D is present), which was obtained in a multi-step synthesis (see Blomquist, J. Org. Chem. 1966, 12, 4121-27). Stogniew also notes that the 5-mono-deutero-glutamine could be obtained through deuterium reduction of 4,5-dihydro-6-carboxy-3(2H)-pyridazone. $D_1$ (1-D) and $D_4$ (2,2,3,3-D) cyclopropane carboxylic acids are commercially available. Cyclopropane-$D_5$-carbonyl chloride is also commercially available.

If non-stereospecific glutamine is used or if the stereospecificity is lost during the reaction, it is expected that the resulting deuterated racemic mixture will be separable using known isolation techniques (e.g., chiral chromatography).

Scheme 2 below provides an exemplary synthetic route for preparing deuterated 2-(2',6'-dioxo-3'-deutero-piperidin-3'-yl)isoindoles.

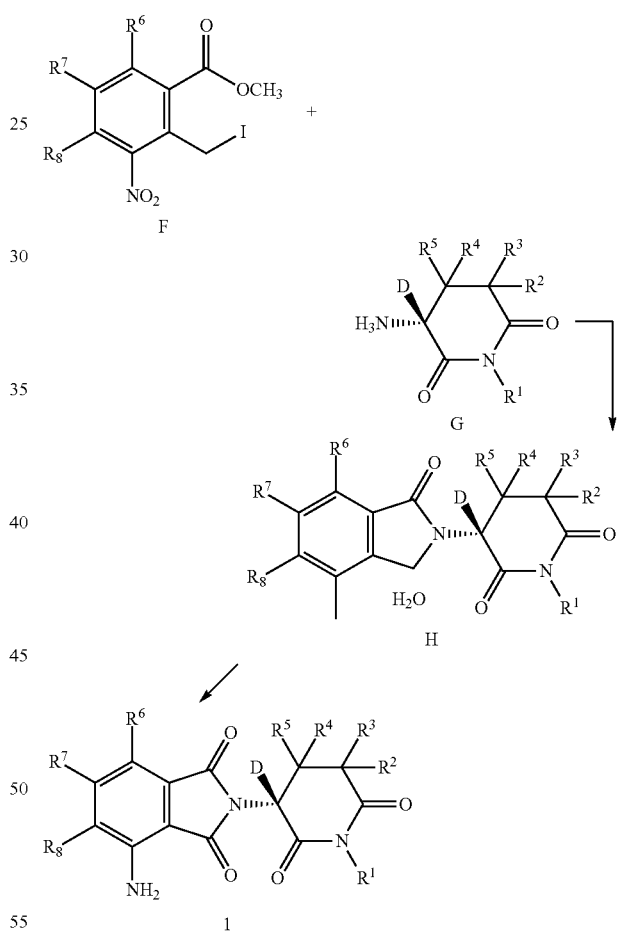

Scheme 2

The compounds of the present invention can also be obtained starting with nitro-benzyl-iodide F, which can be optionally deuterated at the benzylic positions (and the nitro/$R^8$ group can be reversed). Compound F can be reacted with Compound G, an appropriately substituted amino-dioxo-piperidine, typically in the presence of a base (e.g., diisopropylethyl amine in dimethylacetamide) to form Compound H. The 3-deutero group of Compound G is optional as this deuterium is in an acidic position and can be added at a later stage using a base in $D_2O$. The nitro group of Compound H can then be reduced (e.g., hydrogen over 10% Pd—C in methyl alcohol) to form the amino group of Compound I. The amine, if desired, can then be reacted with various groups.

Dosage and Formulation

Dosages of a compound provided herein, or stereoisomer or pharmaceutically acceptable salt thereof, vary depending on factors such as: specific indication to be treated and/or managed; age and condition of a patient; and amount of second active agent used, if any. Generally, a compound provided herein, or stereoisomer or pharmaceutically acceptable salt thereof, may be used in an amount of from about 0.1 mg to about 500 mg per day, and can be adjusted in a conventional fashion {e.g., the same amount administered each day of the treatment and/or management period), in cycles {e.g., one week on, one week off), or in an amount that increases or decreases over the course of treatment and/or management. In other aspects, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. 4.4

Pharmaceutical compositions can be used in the preparation of individual, single unit dosage forms. Pharmaceutical compositions and dosage forms provided herein comprise a compound provided herein, or a pharmaceutically acceptable salt, solvate, stereoisomer, clathrate, or prodrug thereof. Pharmaceutical compositions and dosage forms can further comprise one or more excipients.

Pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., Remington's Pharmaceutical Sciences, 18th ed., Mack Publishing, Easton Pa. (1990).

In another aspect, the present invention the pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, Drug Stability: Principles & Practice, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e powders, tablets, capsules, and caplets) include, but are not limited to, starches, sugars, micro-crystalline cellulose, diluents, granulating agents, lubricants, binders, and disintegrating agents.

In another aspect, the present invention provides oral dosage forms that are tablets or capsules, in which case solid excipients are employed. In another aspect, the tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one aspect, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In another aspect, the present invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat.

Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the present invention procies single unit dosage forms suitable for oral administration such as, but not limited to, tablets, capsules, gelcaps, and caplets that are adapted for controlled-release.

Controlled-release pharmaceutical products improve drug therapy over that achieved by their non-controlled counterparts. In another aspect, the present invention provides the use of a controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

In another aspect, the controlled-release formulations are designed to initially release an amount of drug (active ingredient) that promptly produces the desired therapeutic or prophylactic effect, and gradually and continually release of other amounts of drug to maintain this level of therapeutic or prophylactic effect over an extended period of time. In one aspect, in order to maintain a constant level of drug in the body, the drug can be released from the dosage form at a rate that will replace the amount of drug being metabolized and excreted from the body. Controlle release of an active ingredient can be stimulated by various conditions including, but not limited to, pH, temperature, enzymes, water, or other physiological conditions or compounds.

Parenteral dosage forms can be administered to patients by various routes including, but not limited to, subcutaneous, intravenous (including bolus injection), intramuscular, and intraarterial. Administration of a parenteral dosage form bypasses patients' natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and nonaqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

Topical and mucosal dosage forms provided herein include, but are v"+limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts, solvates, prodrugs, clathrates, or stereoisomers of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the present invention provides a kit comprising a dosage form of a compound provided herein. Kits can further comprise additional active ingredients such as oblimersen (Genasense®), melphalan, G-CSF, GM-CSF, EPO, topotecan, dacarbazine, irinotecan, taxotere, IFN, COX-2 inhibitor, pentoxifylline, ciprofloxacin, dexamethasone, IL2, IL8, IL1 8, Ara-C, vinorelbine, isotretinoin, 13 cis-retinoic acid, or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

Kits can further comprise cells or blood for transplantation as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

EXAMPLES

Table 1 provides compounds that are representative examples of the invention wherein the compound is of formula II and has the specified R groups as deuteriums and the non-specified groups are selected from H and D.

TABLE 1

II

| 1 | $R^1$-$R^{12e}$ = H; |
| 2 | $R^1$-$R^{12e}$ = D; |
| 3 | $R^2$-$R^3$ = D |
| 4 | $R^4$-$R^5$ = D |
| 5 | $R^2$-$R^5$ = D |
| 6 | $R^6$-$R^8$ = D |
| 7 | $R^9$-$R^{10}$ = D |
| 8 | $R^{12a}$ = D |
| 9 | $R^{12b}$-$R^{12e}$ = D |
| 10 | $R^{12a}$-$R^{12e}$ = D |

Table 2 provides compounds that are representative examples of the invention wherein the compound is of formula II and has the specified R groups as deuteriums and the non-specified groups are H.

TABLE 2

| 11 | $R^2$-$R^3$ = D |
| 12 | $R^4$-$R^5$ = D |
| 13 | $R^2$-$R^5$ = D |
| 14 | $R^6$-$R^8$ = D |
| 15 | $R^9$-$R^{10}$ = D |
| 16 | $R^{12a}$ = D |
| 17 | $R^{12b}$-$R^{12e}$ = D |
| 18 | $R^{12a}$-$R^{12e}$ = D |

Table 3 provides compounds that are representative examples of the invention wherein the compound is of formula IIa and has the specified R groups as deuteriums and the non-specified groups are selected from H and D.

TABLE 3

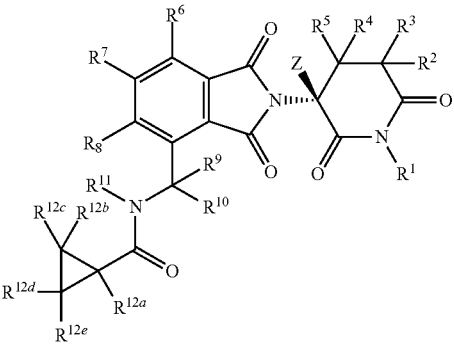

IIa

| 1 | $R^1$-$R^{12e}$ = H; |
| 2 | $R^1$-$R^{12e}$ = D; |
| 3 | $R^2$-$R^3$ = D |
| 4 | $R^4$-$R^5$ = D |
| 5 | $R^2$-$R^5$ = D |
| 6 | $R^6$-$R^8$ = D |
| 7 | $R^9$-$R^{10}$ = D |
| 8 | $R^{12a}$ = D |
| 9 | $R^{12b}$-$R^{12e}$ = D |
| 10 | $R^{12a}$-$R^{12e}$ = D |

Table 4 provides compounds that are representative examples of the invention wherein the compound is of formula IIa and has the specified R groups as deuteriums and the non-specified groups are H.

TABLE 4

| 11 | $R^2$-$R^3$ = D |
| 12 | $R^4$-$R^5$ = D |
| 13 | $R^2$-$R^5$ = D |
| 14 | $R^6$-$R^8$ = D |
| 15 | $R^9$-$R^{10}$ = D |
| 16 | $R^{12a}$ = D |
| 17 | $R^{12b}$-$R^{12e}$ = D |
| 18 | $R^{12a}$-$R^{12e}$ = D |

Table 5 provides compounds that are representative examples of the invention wherein the compound is of formula IIb and has the specified R groups as deuteriums and the non-specified groups are selected from H and D.

TABLE 5

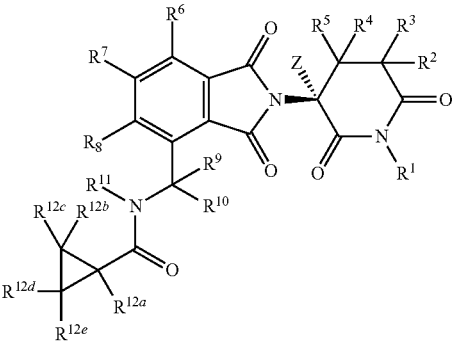

IIb

| 1 | $R^1$-$R^{12e}$ = H; |
| 2 | $R^1$-$R^{12e}$ = D; |
| 3 | $R^2$-$R^3$ = D |
| 4 | $R^4$-$R^5$ = D |
| 5 | $R^2$-$R^5$ = D |

TABLE 5-continued

| 6 | $R^6$-$R^8$ = D |
| 7 | $R^9$-$R^{10}$ = D |
| 8 | $R^{12a}$ = D |
| 9 | $R^{12b}$-$R^{12e}$ = D |
| 10 | $R^{12a}$-$R^{12e}$ = D |

Table 6 provides compounds that are representative examples of the invention wherein the compound is of formula IIb and has the specified R groups as deuteriums and the non-specified groups are H.

TABLE 6

| 11 | $R^2$-$R^3$ = D |
| 12 | $R^4$-$R^5$ = D |
| 13 | $R^2$-$R^5$ = D |
| 14 | $R^6$-$R^8$ = D |
| 15 | $R^9$-$R^{10}$ = D |
| 16 | $R^{12a}$ = D |
| 17 | $R^{12b}$-$R^{12e}$ = D |
| 18 | $R^{12a}$-$R^{12e}$ = D |

Table 7 provides compounds that are representative examples of the invention wherein the compound is of formula I and has the specified R groups as deuteriums and the non-specified groups are selected from H and D.

TABLE 7

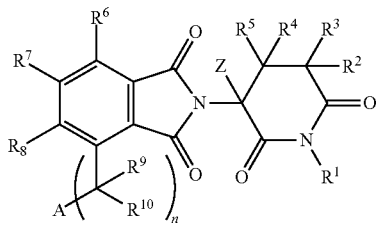

I

| 1 | $R^1$-$R^{12e}$ = H; |
| 2 | $R^1$-$R^{12e}$ = D; |
| 3 | $R^2$-$R^3$ = D |
| 4 | $R^4$-$R^5$ = D |
| 5 | $R^2$-$R^5$ = D |
| 6 | $R^6$-$R^8$ = D |
| 7 | $R^9$-$R^{10}$ = D |
| 8 | $R^{12a}$ = D |
| 9 | $R^{12b}$-$R^{12e}$ = D |
| 10 | $R^{12a}$-$R^{12e}$ = D |

Table 2 provides compounds that are representative examples of the invention wherein the compound is of formula I and has the specified R groups as deuteriums and the non-specified groups are H.

TABLE 2

| 11 | $R^2$-$R^3$ = D |
| 12 | $R^4$-$R^5$ = D |
| 13 | $R^2$-$R^5$ = D |
| 14 | $R^6$-$R^8$ = D |
| 15 | $R^9$-$R^{10}$ = D |
| 16 | $R^{12a}$ = D |
| 17 | $R^{12b}$-$R^{12e}$ = D |
| 18 | $R^{12a}$-$R^{12e}$ = D |

Table 8 provides compounds that are representative examples of the invention wherein the compound is of formula Ic and has the specified R groups as deuteriums and the non-specified groups are selected from H and D.

TABLE 8

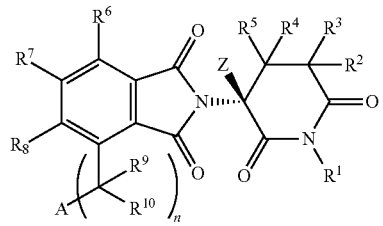

Ic

| 1 | $R^1$-$R^{10}$ and A = H; |
| 2 | $R^1$-$R^{10}$ and A = D; |
| 3 | $R^2$-$R^3$ = D |
| 4 | $R^4$-$R^5$ = D |
| 5 | $R^2$-$R^5$ = D |
| 6 | $R^6$-$R^8$ = D |
| 7 | $R^9$-$R^{10}$ and A = D |

Table 9 provides compounds that are representative examples of the invention wherein the compound is of formula Ic and has the specified R groups as deuteriums and the non-specified groups are H.

TABLE 9

| 8 | $R^1$-$R^{10}$ and A = H; |
| 9 | $R^1$-$R^{10}$ and A = D; |
| 10 | $R^2$-$R^3$ = D |
| 11 | $R^4$-$R^5$ = D |
| 12 | $R^2$-$R^5$ = D |
| 13 | $R^6$-$R^8$ = D |
| 14 | $R^9$-$R^{10}$ and A = D |

Table 10 provides compounds that are representative examples of the invention wherein the compound is of formula Id and has the specified R groups as deuteriums and the non-specified groups are selected from H and D.

TABLE 10

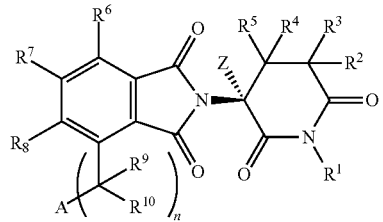

| 1 | $R^1$-$R^{10}$ and A = H; |
| 2 | $R^1$-$R^{10}$ and A = D; |
| 3 | $R^2$-$R^3$ = D |
| 4 | $R^4$-$R^5$ = D |
| 5 | $R^2$-$R^5$ = D |
| 6 | $R^6$-$R^8$ = D |
| 7 | $R^9$-$R^{10}$ and A = D |

Id

Table 11 provides compounds that are representative examples of the invention wherein the compound is of formula Id and has the specified R groups as deuteriums and the non-specified groups are H.

TABLE 11

| 8 | $R^1$-$R^{10}$ and A = H; |
| 9 | $R^1$-$R^{10}$ and A = D; |
| 10 | $R^2$-$R^3$ = D |

TABLE 11-continued

| | |
|---|---|
| 11 | $R^4$-$R^5$ = D |
| 12 | $R^2$-$R^5$ = D |
| 13 | $R^6$-$R^8$ = D |
| 14 | $R^9$-$R^{10}$ and A = D |

Numerous modifications and variations of the invention are possible in light of the above teachings. It is therefore to be understood that within the scope of the appended claims, the invention may be practiced otherwise that as specifically described herein.

What is claimed is:

1. A deuterium-enriched compound of formula II, or a stereoisomer or pharmaceutically acceptable salt thereof:

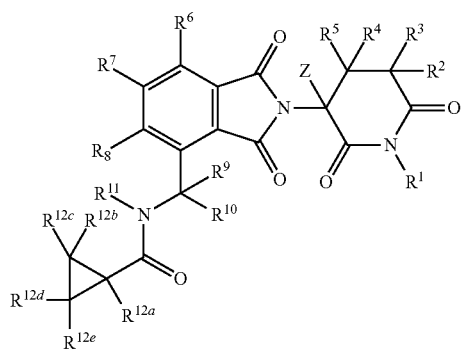

wherein:
Z is H or D, provided that the abundance of deuterium in Z is at least 30%;
$R^1$, $R^2$, $R^3$, $R^4$, $R^5$, $R^6$, $R^7$, $R^8$, $R^9$, $R^{10}$, and $R^{11}$ are independently selected from H and D; and
$R^{12a}$-$R^{12ee}$ are independently selected from H and D.

2. A deuterium-enriched compound of claim 1, wherein the compound is of formula IIa, or pharmaceutically acceptable salt thereof:

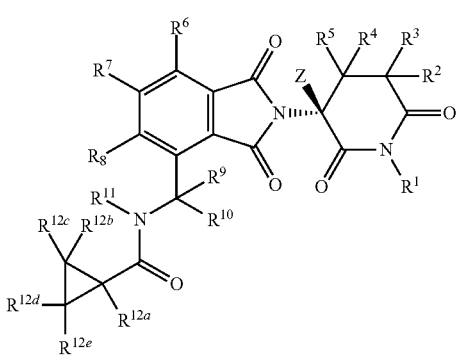

wherein:
$R^{12a}$-$R^{12ee}$ are independently selected from H and D.

3. A deuterium-enriched compound of claim 1, wherein the compound is of formula IIb, or a pharmaceutically acceptable salt thereof:

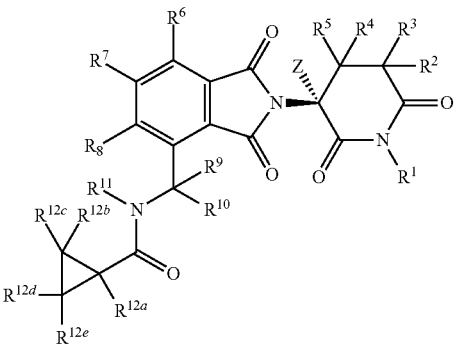

wherein:
$R^{12a}$-$R^{12e}$ are independently selected from H and D.

4. A deuterium-enriched compound of claim 1, wherein the abundance of deuterium in Z is at least 80%.

5. A deuterium-enriched compound of claim 1, wherein the compound is of formula II$_1$, or a stereoisomer or pharmaceutically acceptable salt thereof:

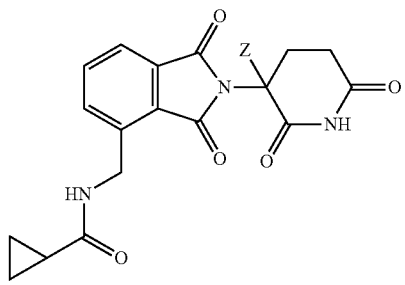

wherein the abundance of deuterium in Z is selected from:
(a) at least 40%, (b) at least 50%, (c) at least 60%, (d) at least 70%, (e) at least 80%, (f) at least 90%, (g) at least 95%, (h) at least 97%, and (i) about 100%.

6. A deuterium-enriched compound of claim 1, wherein the compound is of formula IIa$_1$, or pharmaceutically acceptable salt thereof:

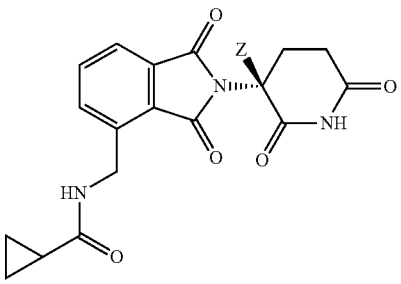

wherein the abundance of deuterium in Z is selected from:
(a) at least 40%, (b) at least 50%, (c) at least 60%, (d) at least 70%, (e) at least 80%, (f) at least 90%, (g) at least 95%, (h) at least 97%, and (i) about 100%.

7. A deuterium-enriched compound of claim 1, wherein the compound is of formula IIb$_1$, or pharmaceutically acceptable salt thereof:

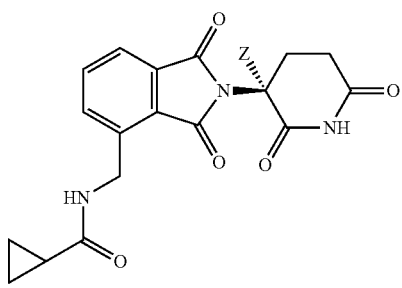

IIb₁ wherein the abundance of deuterium in Z is selected from: (a) at least 40%, (b) at least 50%, (c) at least 60%, (d) at least 70%, (e) at least 80%, (f) at least 90%, (g) at least 95%, (h) at least 97%, and (i) about 100%.

8. A pharmaceutical composition, comprising: a pharmaceutically acceptable carrier and a therapeutically effective amount of a compound of claim 1.

9. A method for treating myelodysplastic syndrome comprising: administering, to a patient in need thereof, a therapeutically effective amount of a compound of claim 1 to treat the myelodysplatic syndrome.

10. The deuterium-enriched compound of claim 5, wherein the compound is a compound of formula II₁ or a stereoisomer thereof.

11. The deuterium-enriched compound of claim 1, wherein the abundance of deuterium in Z is at least 90%.

12. The deuterium-enriched compound of claim 5, wherein the abundance of deuterium in Z is at least 90%.

13. The deuterium-enriched compound of claim 5, wherein the abundance of deuterium in Z is at least 95%.

14. The deuterium-enriched compound of claim 6, wherein the abundance of deuterium in Z is at least 90%.

15. The deuterium-enriched compound of claim 6, wherein the abundance of deuterium in Z is at least 95%.

16. The deuterium-enriched compound of claim 7, wherein the abundance of deuterium in Z is at least 90%.

17. The deuterium-enriched compound of claim 7, wherein the abundance of deuterium in Z is at least 95%.

18. The deuterium-enriched compound of claim 10, wherein the abundance of deuterium in Z is at least 90%.

19. A pharmaceutical composition comprising a compound of claim 5 and one or more excipients.

20. A pharmaceutical composition comprising a compound of claim 11 and one or more excipients.

21. A pharmaceutical composition comprising a compound of claim 12 and one or more excipients.

22. A pharmaceutical composition comprising a compound of claim 14 and one or more excipients.

23. A pharmaceutical composition comprising a compound of claim 16 and one or more excipients.

* * * * *